United States Patent
Kubbutat et al.

(10) Patent No.: US 9,925,193 B2
(45) Date of Patent: Mar. 27, 2018

(54) THIOETHER DERIVATIVES AS PROTEIN KINASE INHIBITORS

(71) Applicant: KTB TUMORFORSCHUNGSGE-SELLSCHAFT MBH, Freiburg (DE)

(72) Inventors: Michael Kubbutat, Schallstadt (DE); Christoph Schachtele, Freiburg (DE); Jan Ehlert, Ehrenkirchen (DE); Frank Totzke, Freiburg (DE); Conrad Kunick, Hamburg (DE); Sebastian Wolfel, Braunschweig (DE); Holger Weber, Freiburg (DE)

(73) Assignee: ProQinase GmbH, Freiburg (DE)

( * ) Notice: Subject to any disclaimer, the term of this patent is extended or adjusted under 35 U.S.C. 154(b) by 0 days.

(21) Appl. No.: 14/646,252

(22) PCT Filed: Nov. 11, 2013

(86) PCT No.: PCT/EP2013/003387
§ 371 (c)(1),
(2) Date: May 20, 2015

(87) PCT Pub. No.: WO2014/079545
PCT Pub. Date: May 30, 2014

(65) Prior Publication Data
US 2015/0328219 A1    Nov. 19, 2015

(30) Foreign Application Priority Data

Nov. 20, 2012  (EP) ..................................... 12007825
Aug. 1, 2013   (EP) ..................................... 13003832
Oct. 8, 2013   (EP) ..................................... 13004832

(51) Int. Cl.
| | |
|---|---|
| C07D 495/04 | (2006.01) |
| A61K 31/519 | (2006.01) |
| A61K 31/52 | (2006.01) |
| A61K 31/5377 | (2006.01) |
| A61K 31/55 | (2006.01) |
| A61P 35/00 | (2006.01) |
| A61P 35/02 | (2006.01) |
| A61P 35/04 | (2006.01) |
| A61P 29/00 | (2006.01) |
| A61P 37/00 | (2006.01) |

(52) U.S. Cl.
CPC ............ *A61K 31/52* (2013.01); *A61K 31/519* (2013.01); *A61K 31/5377* (2013.01); *A61K 31/55* (2013.01); *C07D 495/04* (2013.01)

(58) Field of Classification Search
CPC ............................ A61K 31/519; C07D 495/04
See application file for complete search history.

(56) References Cited

U.S. PATENT DOCUMENTS

| | | |
|---|---|---|
| 2,628,235 A | 2/1953 | Hitchings et al. |
| 3,573,309 A | 3/1971 | Bergmann et al. |
| 5,021,574 A | 6/1991 | Hajos et al. |
| 7,427,616 B2 * | 9/2008 | Luke .................. C07D 473/34 |
| | | 514/230.5 |

FOREIGN PATENT DOCUMENTS

| | | |
|---|---|---|
| EP | 1444982 A1 | 6/2003 |
| WO | 2004013141 A1 | 2/2004 |
| WO | 2007054831 A2 | 5/2007 |
| WO | 2008041053 A2 | 4/2008 |
| WO | 2008124083 A2 | 10/2008 |
| WO | 2010090764 A1 | 8/2010 |
| WO | 2011072275 A2 | 6/2011 |

OTHER PUBLICATIONS

STN search, Aug. 19, 2016, p. 1.*
Yike, Ni et al., "Identification and SAR of a New Series of thieno[3,2-d]pyrimidines as Tpl2 Kinase Inhibitors," Bioorganic & Medicinal Chemistry Letters, 2011, vol. 21 (19): 5952-5956.
Ibrahim, Nada et al., "Novel 8-arylated Purines as Inhibitors of Glycogen Synthase Kinase," European Journal of Medicinal Chemistry, 2010, vol. 45(8): 3389-3393.
RN927063-57-8, Mar. 18, 2007.
RN927151-35-7, Mar. 18, 2007.
RN1014515-85-5. Apr. 15, 2008.

* cited by examiner

*Primary Examiner* — Susanna Moore
(74) *Attorney, Agent, or Firm* — Stinson Leonard Street LLP

(57) ABSTRACT

The present invention relates to thioether derivatives (1) as protein kinase inhibitors, which are useful for the treatment, relieve and/or prevention of diseases associated with abnormal and hyperproliferation of cells in a mammal, especially humans, and which are particularly useful for the treatment of all forms of cancer.

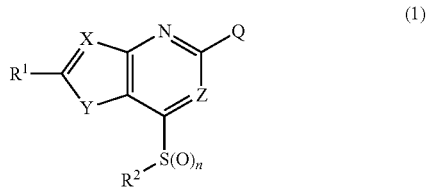

(1)

7 Claims, No Drawings

THIOETHER DERIVATIVES AS PROTEIN KINASE INHIBITORS

This application claims priority to International Publication Number WO 2014/079545, filed on Nov. 11, 2013, which claims priority to European Patent Application No. 13004832, filed on Oct. 8, 2013, European Patent Application No. 13003832, filed on Aug. 1, 2013, and European Patent Application No. 12007825, filed on Nov. 20, 2012, each of which are hereby incorporated by reference herein in their entireties.

The present invention relates to thioether derivatives as protein kinase inhibitors, which are useful for the treatment, relieve and/or prevention of diseases associated with abnormal and hyperproliferation of cells in a mammal, especially humans, and which are particularly useful for the treatment of all forms of cancer.

Protein kinases play a central role in the regulation of cellular functions. This includes processes like cell growth and division, cell differentiation and cell death, but also many other cellular activities. Protein kinases catalyze the transfer of phosphate residues from ATP on target proteins which, as a consequence of this protein kinase mediated phosphorylation, change their three-dimensional structure and thereby their physiological function. Depending on the amino acid which is phosphorylated by a protein kinase, these enzymes are grouped in two families, the so-called serine/threonine protein kinases and the tyrosine protein kinases.

Based on the human genome project, it is known that in human beings there exist 518 DNA sequences which encode for a protein kinase-like protein sequence. For several of these 518 proteins it could be shown in the last about 20 years that modifications in their related gene sequences (e.g. point mutations, deletions or gene amplifications) result in pathological changes of the cellular activities of the corresponding protein kinase. This is particularly true for protein kinases which are involved in cell proliferation and cell cycle control, in survival of cells and cell death, in tumor angiogenesis, and in formation of tumor metastases.

Several so-called oncogenes are pathologically modified genes which in their proto-oncogenic form encode for protein kinases involved in normal, physiological regulation of cell growth and division.

Since protein kinases are key regulators of cell functions and since they can show dysregulated enzymatic activity in cells, they are promising targets for the development of therapeutic agents. There are many ongoing drug discovery projects in the pharmaceutical industry with the goal to identify modulators of protein kinases. The major focus is currently on protein kinases involved in inflammation and cancer, but besides this, protein kinases are currently discussed as promising targets in almost every area of diseases.

In the field of tumors, the first protein kinase inhibitors (e.g. Gleevec, Iressa) have already reached the market. In addition, a great number of protein kinase inhibitors are currently in various phases of clinical development. In most cases, these compounds are either targeting subtypes of the EGF (Epidermal Growth Factor) receptor or of the VEGF (Vascular Endothelial Growth Factor) receptor. All these compounds have been developed with the goal to specifically inhibit one particular protein kinase, for which there is evidence that it interferes with one of the four major molecular processes of tumor progression. These four processes are (a) cell proliferation/cell cycle control, (b) regulation of programmed cell death (apoptosis) and cell survival, (c) tumor angiogenesis and (d) tumor metastasis.

Considering the lack of currently available treatment options for the majority of the conditions associated with protein kinases like ALK, AXL, FAK, IGF1-R, SRC, and VEGF-R2, especially with protein kinases like ALK (cell proliferation), AXL (apoptosis), FAK (metastasis), VEGF-R2 (angiogenesis), there is still a great medical need for new therapeutic agents that inhibit these protein targets.

Accordingly, the technical problem underlying the present invention is to provide a protein kinase inhibitor that can inhibit protein kinases like ALK, AXL, FAK, IGF1-R, SRC and VEGF-R2, and which can be used in the treatment, relieve and/or prevention of a disease, particularly of all forms of cancer.

The solution to the above technical problem is achieved by the embodiments characterized in the claims.

In particular, the present invention provides thioether derivatives as protein kinase inhibitors which are useful for inhibition of protein kinases involved in diseases besides cancer, but which are especially useful as anti-tumor agents. This includes monospecific protein kinase inhibitors, which preferentially inhibit one protein kinase which is causatively involved in tumor progression, but also so-called multi-target protein kinase inhibitors, which inhibit at least two different protein kinases which play a role in two or more different molecular mechanisms of tumor progression. As an example, such a compound could be an inhibitor of tumor angiogenesis and, in addition, also a stimulator of apoptosis. The concept of multi-target protein kinase inhibitors is a new approach, although the idea of developing "multiplex protein kinase inhibitors" has already been described by J. Adams et al., Current Opinion in Chemical Biology 6, 486-492, 2002. Therein compounds are described, which, at the same time, inhibit several protein kinases, which however all are involved in one molecular mechanism of tumor progression, namely tumor angiogenesis. The present invention now provides thioether derivatives as a new group of protein kinase inhibitors which show differential inhibition of protein kinases, each of which can be assigned to one of the four molecular mechanisms of tumor development.

According to one aspect of the present invention, there is provided a protein kinase inhibitor according to general formula (1) or a pharmaceutically acceptable salt thereof:

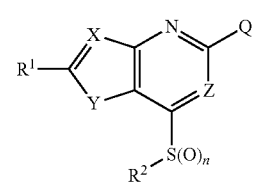

Formula (1)

wherein X is selected from N and CH;
Y is selected from NH, S and O;
Z is selected from N and CH;
$R^1$ is selected from a substituted or unsubstituted aryl group and a substituted or unsubstituted heteroaryl group;
$R^2$ is selected from a substituted or unsubstituted alkyl group, a substituted or unsubstituted aryl group and a substituted or unsubstituted heteroaryl group;
n is selected from 0, 1 and 2; and
Q is selected from H and a substituted or unsubstituted amino group.

X, Y, Z, n and the residues $R^1$, $R^2$ and Q in the above general formula (1) can be selected independently of each other.

The index "n" in the above general formula (1) is selected from 0, 1 and 2. According to a preferred embodiment of the present invention, n in the above general formula (1) is 0.

"Q" in the above general formula (1) is selected from H (hydrogen) and a substituted or unsubstituted amino group. In the present invention, an unsubstituted amino group is a —NH$_2$ group. The amino group may optionally be substituted, i.e. one or both hydrogen atom(s) of the amino group may be replaced by a substituent. Such substituents may be e.g. alkyl (to form a monoalkylamino or a dialkylamino group), alkenyl, alkylidene, alkynyl, aryl, arylidene, acyl, cycloalkyl, heteroaryl, heteroarylidene, etc. In case both hydrogen atoms of the amino group are replaced by a substituent, the substituents can be selected independently of each other. According to a preferred embodiment of the present invention, Q in the above general formula (1) is H.

"X" in the above bicyclic ring system of general formula (1) is selected from N (nitrogen) and CH. According to a preferred embodiment of the present invention, X in the above general formula (1) is CH. According to another preferred embodiment of the present invention, X in the above general formula (1) is N.

"Y" in the above bicyclic ring system of general formula (1) is selected from NH, S (sulphur) and O (oxygen). According to a preferred embodiment of the present invention, Y in the above general formula (1) is S. According to another preferred embodiment of the present invention, Y in the above general formula (1) is NH.

"Z" in the above bicyclic ring system of general formula (1) is selected from N (nitrogen) and CH. According to a preferred embodiment of the present invention, Z in the above general formula (1) is N.

According to a particularly preferred embodiment of the present invention, n is 0, Q is H, X is CH, Y is S, and Z is N at the same time in the above general formula (1), thereby forming a thieno[3,2-d]pyrimidine derivative of the general formula (2).

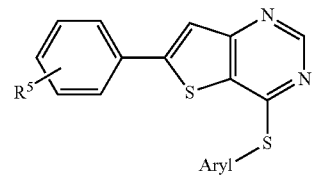

Formula (2)

According to another particularly preferred embodiment of the present invention, n is 0, Q is H, X is N, Y is NH, and Z is N at the same time in the above general formula (1), thereby forming a purine derivative of the general formula (2a).

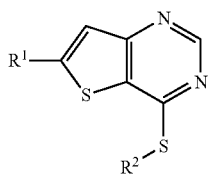

Formula (2a)

In this context, it should be noted that the compound of the general formula (2a) is in a tautomeric equilibrium with compound (2a*), said tautomeric compound (2a*) also being encompassed by the present invention. The same applies for all specifically exemplified compounds mentioned herein.

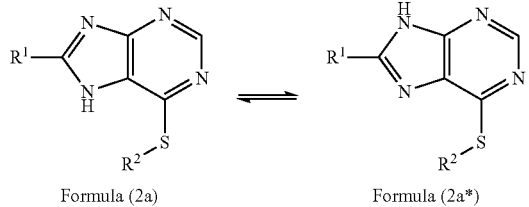

Formula (2a)          Formula (2a*)

$R^1$ in the above general formulas (1), (2), (2a) and (2a*) is selected from a substituted or unsubstituted aryl group and a substituted or unsubstituted heteroaryl group.

According to a specific embodiment, the thieno[3,2-d]pyrimidine derivative of the general formula (2) is a compound represented by the following formula:

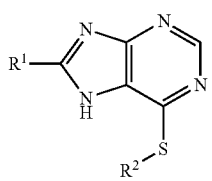

wherein the substituent(s) $R^5$ is/are not particularly limited and may be e.g. alkyl, halogen, aryl, heteroaryl, hydroxyl, alkoxy, carboxylic acids and derivatives thereof, acyl, amino, alkylamino, cyano, nitro, alkylsulfanyl, alkylsulfinyl, alkylsulfonyl, sulfamoyl, sulfoximino, trihalogenmethoxy, trihalogenmethyl, etc. In case of two or more substituents $R^5$, the two or more substituents $R^5$ may be the same or different. The position of the substituent(s) in the aryl group is not particularly limited. For example, the phenyl group may be substituted in the ortho-, meta- and/or para-position(s).

In the present invention, "aryl" refers to any aromatic hydrocarbon group, e.g. a phenyl group, a naphthyl group, etc. The aryl group may optionally be (poly)substituted, i.e. one or more hydrogen atom(s) of the aryl group may be replaced by a substituent. Such substituents may be e.g. alkyl, halogen, aryl, heteroaryl, hydroxyl, alkoxy, carboxylic acids and derivatives thereof, acyl, amino, alkylamino, cyano, nitro, alkylsulfanyl, alkylsulfinyl, alkylsulfonyl, sulfamoyl, sulfoximino, trihalogenmethoxy, trihalogenmethyl, etc. The position of the substituent(s) in the aryl group is not particularly limited. For example, a phenyl group may be substituted in the ortho-, meta- and/or para-position(s).

In the present application, "heteroaryl" refers to any monocyclic or bicyclic aromatic hydrocarbon group in which one or more carbon atom(s) is/are replaced by a heteroatom such as e.g. nitrogen, oxygen, sulphur, etc. In case two or more carbon atoms are replaced by a heteroatom, the heteroatoms may be the same or different. Heteroaryl groups in the present invention are e.g. benzofuryl, benzimidazolyl, benzisoxazolyl, benzothiazolyl, cinnolinyl, furyl, imidazolyl, indazolyl, indolizinyl, indolyl, isoindolyl, isoquinolyl, isoxazolyl, naphthyridyl, oxadiazolyl, oxazolyl, phthalazinyl, pyrazolyl, pyrazinyl, pyridazinyl, pyridinyl pyrimidinyl, quinazolyl, quinolyl, quinoxalyl, thiazolyl, tetrazolyl, thiadiazolyl, triazolyl, etc. The position of attachment at the heteroaryl group to the bicyclic ring system of the general formula (1) is not particularly limited. The heteroaryl group may optionally be (poly)substituted, i.e. one or more hydrogen atom(s) of the heteroaryl group may be replaced by a substituent. Such substituents may be e.g. alkyl, halogen, aryl, heteroaryl, hydroxyl, alkoxy, carboxylic acids and derivatives thereof, acyl, amino, alkylamino, cyano, nitro, alkylsulfanyl, alkylsulfinyl, alkylsulfonyl, sulfamoyl, sulfoximino, trihalogenmethoxy, trihalogenmethyl, etc. The position of the substituent(s) in the heteroaryl group is not particularly limited.

According to a preferred embodiment of the present invention, $R^1$ in the above general formulas (1) and (2) is the following residue:

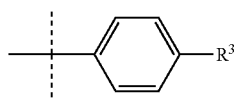

$R^3$ in the above residue may be a halogen atom such as F (fluorine), Cl (chlorine), Br (bromine) and I (iodine).

Alternatively, $R^3$ in the above residue may be a substituted or unsubstituted alkyl group. The alkyl group may be linear or branched. In the present invention, "linear alkyl" refers to a linear hydrocarbon group such as methyl, ethyl, propyl, etc. The chain length of the linear alkyl group is not particularly limited. However, a chain length of $C_1$-$C_6$ is preferable. In the present invention, "branched alkyl" refers to a branched hydrocarbon group such as iso-propyl, sec-butyl, tert-butyl, etc. The number of carbon atoms constituting the branched alkyl group is not particularly limited. However, a number of carbon atoms of $C_3$-$C_6$ is preferable. The linear or branched alkyl group may optionally be (poly)substituted, i.e. one or more hydrogen atom(s) of the alkyl group may be replaced by a substituent. Such substituents may be e.g. halogen, aryl, heteroaryl, hydroxyl, alkoxy, carboxylic acids and derivatives thereof, acyl, amino, alkylamino, cyano, nitro, alkylsulfanyl, alkylsulfinyl, alkylsulfonyl, sulfamoyl, sulfoximino, trihalogenmethoxy, trihalogenmethyl, etc.

Alternatively, $R^3$ in the above residue may be a hydroxyl (—OH). Moreover, the hydrogen atom of the hydroxyl group may be substituted to form an alkoxy. The substituent may be e.g. a linear or branched alkyl, cycloalkyl, aryl, heteroaryl, etc., and one or more hydrogen atoms of the substituent may further be substituted by e.g. alkyl, halogen, aryl, heteroaryl, hydroxyl, alkoxy, carboxylic acid or derivatives thereof.

According to a preferred embodiment of the present invention, $R^3$ in the above residue is F (fluorine).

According to a preferred embodiment of the present invention, $R^1$ in the above general formulas (2a) and (2a*) is a phenyl group.

$R^2$ in the above general formulas (1), (2), (2a) and (2a*) is selected from a substituted or unsubstituted alkyl group, a substituted or unsubstituted aryl group and a substituted or unsubstituted heteroaryl group. The definitions of "substituted or unsubstituted alkyl group", "substituted or unsubstituted aryl group" and "substituted or unsubstituted heteroaryl group" are the same as provided above with respect to the residues $R^1$ and $R^3$.

According to a preferred embodiment of the present invention, $R^2$ is the following residue:

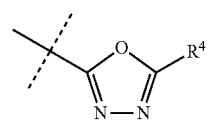

wherein $R^4$ is selected from amino, monoalkylamino, dialkylamino, alkoxy, substituted or unsubstituted alkyl, substituted or unsubstituted cycloalkyl having one or more heteroatoms, substituted or unsubstituted aryl, substituted or unsubstituted heteroaryl, substituted sulfanyl (—SR'), sulfinyl (—S(O)R'), sulfonyl (—S(O)$_2$R'), sulfamoyl (—S(O)$_2$NH$_2$) and sulfoximino (—S(O)(NH)R'), wherein R' is e.g. a substituted or unsubstituted alkyl/alkenyl/alkinyl/cycloalkyl group, an aryl group, etc. The definitions of "substituted or unsubstituted alkyl", "substituted or unsubstituted aryl", "substituted or unsubstituted heteroaryl", "amino", "monoalkylamino", "dialkylamino" and "alkoxy" are the same as defined above with respect to the residues $R^1$, $R^2$ and $R^3$.

Alternatively, $R^4$ in the above residue may be a substituted or unsubstituted cycloalkyl group. In the present invention, "cycloalkyl" refers to a cyclic hydrocarbon group such as cyclopropyl, cyclobutyl, cyclopentyl, etc. The cycloalkyl group may optionally contain one or more double and/or triple bond(s), and may optionally be (poly)substituted, i.e. one or more hydrogen atom(s) of the cycloalkyl group may be replaced by a substituent. Such substituents may be e.g. halogen, aryl, heteroaryl, hydroxyl, alkoxy, carboxylic acids and derivatives thereof, acyl, amino, alkylamino, cyano, nitro, alkylsulfanyl, alkylsulfinyl, alkylsulfonyl, sulfamoyl, sulfoximino, trihalogenmethoxy, trihalogenmethyl, etc. Moreover, one or more carbon atom(s) of the cycloalkyl group may be replaced by a heteroatom such as e.g. nitrogen, oxygen, sulphur, etc. In case two or more carbon atoms are replaced by a heteroatom, the heteroatoms may be the same or different.

According to a preferred embodiment, $R^4$ is selected from substituted or unsubstituted alkyl, substituted or unsubstituted cycloalkyl having one or more heteroatoms, substituted or unsubstituted aryl and substituted or unsubstituted heteroaryl.

Particularly preferable examples of $R^4$ include a substituted or unsubstituted phenyl group, a pyridinyl group, an amino substituted alkyl group, a heterocyclyl substituted alkyl group, and a substituted or unsubstituted benzyl group.

According to a particularly preferred embodiment of the present invention, the protein kinase inhibitor is a compound having the general formula (3) or a pharmaceutically acceptable salt thereof:

Formula (3)

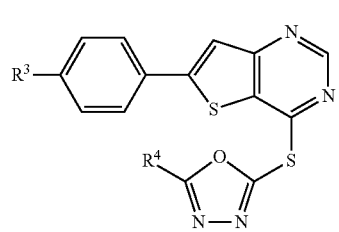

wherein $R^3$ and $R^4$ are independent of each other as defined above.

According to another particularly preferred embodiment of the present invention, the protein kinase inhibitor is a compound having the general formula (3a) or a tautomeric compound thereof or a pharmaceutically acceptable salt thereof:

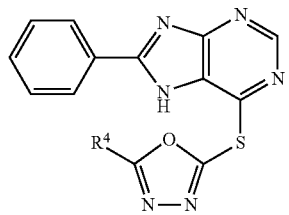

Formula (3a)

wherein R⁴ is as defined above.

The protein kinase inhibitor according to the present invention may be the thioether derivative as described above or a pharmaceutically salt thereof. In case the protein kinase inhibitor of the present invention is a pharmaceutically acceptable salt of the thioether derivative according to general formula (1), the salt can be formed with inorganic or organic acids or bases. Examples of pharmaceutically acceptable salts comprise, without limitation, non-toxic inorganic or organic salts such as acetate derived from acetic acid, aconitate derived from aconitic acid, ascorbate derived from ascorbic acid, benzoate derived from benzoic acid, cinnamate derived from cinnamic acid, citrate derived from citric acid, embonate derived from embonic acid, enantate derived from heptanoic acid, formiate derived from formic acid, fumarate derived from fumaric acid, glutamate derived from glutamic acid, glycolate derived from glycolic acid, chloride derived from hydrochloric acid, bromide derived from hydrobromic acid, lactate derived from lactic acid, maleate derived from maleic acid, malonate derived from malonic acid, mandelate derived from mandelic acid, methanesulfonate derived from methanesulfonic acid, naphtaline-2-sulfonate derived from naphtaline-2-sulfonic acid, nitrate derived from nitric acid, perchlorate derived from perchloric acid, phosphate derived from phosphoric acid, phthalate derived from phthalic acid, salicylate derived from salicylic acid, sorbate derived from sorbic acid, stearate derived from stearic acid, succinate derived from succinic acid, sulphate derived from sulphuric acid, tartrate derived from tartaric acid, toluene-p-sulfonate derived from p-toluenesulfonic acid and others. Such salts can be readily produced by methods known to a person skilled in the art.

Other salts like oxalate derived from oxalic acid, which is not considered as pharmaceutically acceptable, can be appropriate as intermediates for the production of the protein kinase inhibitor of the general formula (1) or a pharmaceutically acceptable salt thereof or physiologically functional derivative or a stereoisomer thereof.

In a further aspect, the present invention relates to the use of the protein kinase inhibitor as defined above in medicine.

In particular, the present invention relates to the use of the protein kinase inhibitor as defined above in the treatment, relieve and/or prevention of a disease selected from cell proliferation disorders, cardiovascular disorders, immunological diseases, inflammatory diseases, neuroimmunological diseases, neurodegenerative disorders, autoimmune diseases. The treatment, relieve and/or prevention of the above diseases is preferably in a mammal, more preferably in a human.

"Treatment" according to the present invention is intended to mean complete or partial healing of a disease, or alleviation of a disease or stop of progression of a given disease.

In one embodiment, the protein kinase inhibitor as defined above is used for the treatment of diseases which are caused by malignant cell proliferation, such as all forms of solid tumors, leukemias and lymphomas. Therefore, the protein kinase inhibitor as defined above, as well as pharmaceutical compositions prepared therewith, is used for regulating cell activation, cell proliferation, cell survival, cell differentiation, cell cycle, cell maturation and cell death or to induce systemic changes in metabolism such as changes in sugar, lipid or protein metabolism. The protein kinase inhibitor as defined above can also be used to support cell generation poiesis, including blood cell growth and generation (prohematopoietic effect) after depletion or destruction of cells, as caused by e.g. toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis, or blood vessel or lymphatic vessel formation or growth.

According to a preferred embodiment of the present invention, the protein kinase inhibitor as defined above is used in the treatment, relieve and/or prevention of cancer. The cancer may be hematological (e.g. leukemia, lymphoma, myeloma) or solid tumors (e.g. breast, prostate, liver, bladder, lung, esophageal, stomach, colorectal, genitourinary, gastrointestinal, skin, pancreatic, brain, uterine, colon, head and neck, cervical, and ovarian, melanoma, astrocytoma, small cell lung cancer, non small cell lung cancer, glioma, basal and squameous cell carcinoma, sarcomas as Kaposi's sarcoma and osteosarcoma).

According to a particular preferred embodiment of the present invention, the cancer is a solid tumor in breast, bladder, colorectal, lung, prostate, pancreatic and renal cancer, or leukemias or lymphomas (such as e.g. anaplastic large cell lymphoma).

In another embodiment of the present invention, the protein kinase inhibitor as defined above is used for treating, relieving, and/or preventing diseases in which cell proliferation disorders play a role.

In a preferred embodiment of the present invention, the protein kinase inhibitor as defined above is used for treating, relieving, and/or preventing diseases by inhibition of one ore more protein kinases and/or phosphatases.

In a particularly preferred embodiment of the present invention, the protein kinase inhibitor as defined above is used for treating, relieving, and/or preventing diseases by inhibition of one or more kinases, such as ALK, AXL, FAK, IGF1-R, SRC, and VEGF-R2.

In another embodiment of the present invention, the protein kinase inhibitor as defined above is used for treating, relieving and/or preventing diseases in which T cells play a role, especially inflammatory disorders and immune disorders such as Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Crohn's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, autoimmune demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Harnman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoriasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antibodies, thrombocytopenia, idiopathic thrombocytopenia purpura, thymoma, acute anterior uveitis, vitiligo, AIDS, HIV, SCID and Epstein Barr virus associated diseases such as Sjörgren's syndrome, virus (AIDS or EBV) associated B cell lymphoma, parasitic diseases such as Leishmania, and immunesuppressed disease states such as viral infections following allograft transplantations, AIDS, cancer, chronic active hepatitis diabetes, toxic chock syndrome and food poisoning.

According to another embodiment of the present invention, the protein kinase inhibitor as defined above is used for treating, relieving and/or preventing diseases that are caused by protozoal infestations in humans and animals. Such veterinary and human pathogenic protozoas are preferably intracellular active parasites of the phylum Apicomplexa or Sarcomastigophora, especially *Trypanosoma, Plasmodia, Leishmania, Babesia* and *Theileria, Cryptosporidia, Sarcocystida, Amoebia, Coccidia* and *Trichomonadia*. The protein kinase inhibitor as defined above is particularly suitable for the treatment of Malaria tropica, caused by *Plasmodium falciparum*, Malaria tertiana, caused by *Plasmodium vivax* or *Plasmodium ovale* and for the treatment of Malaria quartana, caused by *Plasmodium malariae*. The protein kinase inhibitor as defined above is also suitable for the treatment of Toxoplasmosis, caused by *Toxoplasma gondii*, Coccidiosis, caused for instance by *Isospora belli*, intestinal Sarcosporidiosis, caused by *Sarcocystis suihominis*, dysentery caused by *Entamoeba histolytica*, Cryptosporidiosis, caused by *Cryptosporidium parvum*, Chagas' disease, caused by *Trypanosoma cruzi*, sleeping sickness, caused by *Trypanosoma brucei rhodesiense* or *gambiense*, the cutaneous and visceral as well as other forms of Leishmaniosis. The protein kinase inhibitor as defined above is also suitable for the treatment of animals infected by veterinary pathogenic protozoa, like *Theileria parva*, the pathogen causing bovine East coast fever, *Trypanosoma congolense congolense* or *Trypanosoma vivax vivax, Trypanosoma brucei brucei*, pathogens causing Nagana cattle disease in Africa, *Trypanosoma brucei evansi* causing Surra, *Babesia bigemina*, the pathogen causing Texas fever in cattle and buffalos, *Babesia bovis*, the pathogen causing European bovine Babesiosis as well as Babesiosis in dogs, cats and sheep, *Sarcocystis ovicanis* and *ovifelis* pathogens causing Sarcocystiosis in sheep, cattle and pigs, Cryptosporidia, pathogens causing Cryptosporidioses in cattle and birds, *Eimeria* and *Isospora* species, pathogens causing Coccidiosis in rabbits, cattle, sheep, goats, pigs and birds, especially in chickens and turkeys. The protein kinase inhibitor as defined above is particularly preferred for use in the treatment of Coccidiosis or Malaria infections, or for the preparation of a drug or feed stuff for the treatment of these diseases.

This treatment can be prophylactic or curative. In the treatment of malaria, the protein kinase inhibitor as defined above may be combined with other anti-malaria agents.

The protein kinase inhibitor as defined above may further be used for viral infections or other infections caused e.g. by *Pneumocystis carinii*.

Furthermore, the present invention relates to a method of treatment or prevention of diseases, which comprises the administration of an effective amount of the protein kinase inhibitor as defined above or a pharmaceutically acceptable salt thereof.

The protein kinase inhibitor as defined above and the pharmacologically acceptable salts thereof can be administered to animals, preferably to mammals, and in particular to humans, dogs and chickens as therapeutics per se, as mixtures with one another or in the form of pharmaceutical preparations which allow enteral or parenteral use, and which as active constituent contains an effective dose of at least one protein kinase inhibitor as defined above or a pharmaceutically acceptable salt thereof, in addition to customary pharmaceutically innocuous excipients and additives. The protein kinase inhibitor as defined above can also be administered in form of its salts, which are obtainable by reacting the respective compounds with physiologically acceptable acids and bases.

The production of medicaments containing the protein kinase inhibitor as defined above and its application can be performed according to well-known pharmaceutical methods.

While the protein kinase inhibitor as defined above for use in therapy may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the protein kinase inhibitor as defined above may be anhydrous or solvated.

In a preferred embodiment, the invention provides medicaments comprising protein kinase inhibitor as defined above, or a pharmaceutically acceptable salt or physiologically functional derivative or a stereoisomer thereof, together with one or more pharmaceutically acceptable carriers thereof, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The protein kinase inhibitor as defined above, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The protein kinase inhibitor as defined above can be administered in a wide variety of oral and parenteral dosage forms. It will be obvious to those skilled in the art that the following dosage forms may comprise, as the active component, either the protein kinase inhibitor as defined above or a pharmaceutically acceptable salt or stereoisomer thereof.

For preparing a medicament from the protein kinase inhibitor as defined above, pharmaceutically acceptable carriers can be either solid or liquid. Solid form preparations include powders, tablets, pills, capsules, cachets, lozenges, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The protein kinase inhibitor as defined above may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

In a particularly preferred embodiment of the present invention, the medicament is applied topically. This reduces possible side effects and limits the necessary treatment to those areas affected.

Preferably the medicament is prepared in form of an ointment, a gel, a plaster, an emulsion, a lotion, a foam, a cream of a mixed phase or amphiphilic emulsion system (oil/water-water/oil mixed phase), a liposome, a transfersome, a paste or a powder.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively, the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form, for example in capsules or cartridges of e.g. gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Pharmaceutical compositions can also contain two or more protein kinase inhibitors as defined above or their pharmacologically acceptable salts and also other therapeutically active substances.

Thus, the protein kinase inhibitor as defined above can be used in the form of one compound alone or in combination with other active compounds—for example with medicaments already known for the treatment of the aforementioned diseases, whereby in the latter case a favorable additive, amplifying effect is noticed. Suitable amounts to be administered to humans range from 5 to 1,250 mg per day.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight preferably 1 to 50 mg/kg. Suitable dosage rates for larger mammals, for example humans, are of the order of from about 10 mg to 3 g/day, conveniently administered once, in divided doses such as e.g. 2 to 4 times a day, or in sustained release form.

In general, a daily dose of approximately 10 mg to 5000 mg, preferably 50 to 500 mg, per human individual is appropriate in the case of the oral administration. In the case of other administration forms too, the daily dose is in similar ranges. For topical delivery, depending on the permeability of the skin, the type and the severity of the disease and dependent on the type of formulation and frequency of application, different concentrations of active compounds within the medicament can be sufficient to elicit a therapeutic effect by topical application. Preferably, the concentration of an active compound or a pharmaceutically acceptable salt thereof or a physiologically functional derivative or a stereoisomer thereof within a medicament according to the invention is in the range of between 1 µmol/L and 100 mmol/L.

Another aspect of the present application relates to a method for producing the protein kinase inhibitor according to general formula (4):

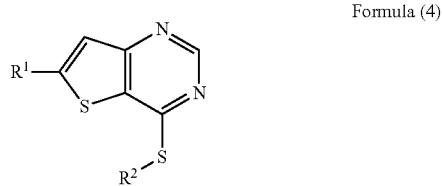

Formula (4)

wherein the method comprises reacting a compound of general formula (5):

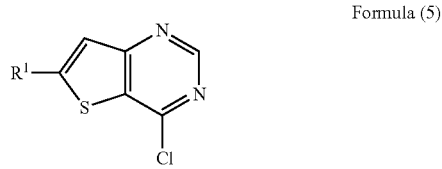

Formula (5)

with $R^2$—SH in the presence of a base.

In the above formulas (4) and (5), $R^1$ and $R^2$ are the same as defined above for formulas (1) and (2). According to a preferred embodiment, $R^1$ is a substituted phenyl group, e.g the following residue

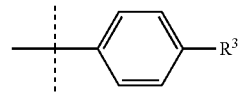

in which $R^3$ is the same as defined above.

The base in the above method is not particularly limited. According to a preferred embodiment, the base is N,N-diisopropylmethylamine, potassium carbonate or sodium hydroxide. The base is used in at least equimolar amount with respect to the compound $R^2$—SH. Preferably, 1.5 equivalents of base are used with respect to the compound $R^2$—SH.

The solvent in the above method is not particularly limited. According to a preferred embodiment, the solvent is n-butanol, acetonitrile or ethanol. The above method is preferably carried out at a temperature of at least 90° C., while the reaction time is preferably at least six hours when carried out by conventional heating, e.g. by means of an oil bath or a similar heat source. The above method is alternatively preferably carried out at a temperature of at least 60° C., while the reaction time is preferably at least 10 min when carried out in a microwave oven for chemical syntheses. After the reaction is complete, the reaction mixture is worked-up according to standard methods known to a person skilled in the art. For example, the solvent is evaporated and the residue is recrystallized from a solvent, e.g. toluene, to yield the product of general formula (4).

Further, a starting material of the general formula (6):

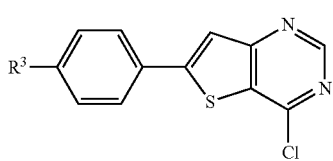

Formula (6)

useful for the above method may e.g. be prepared by the following reaction sequence, wherein the individual steps are according to references [1], [3] and [4]:

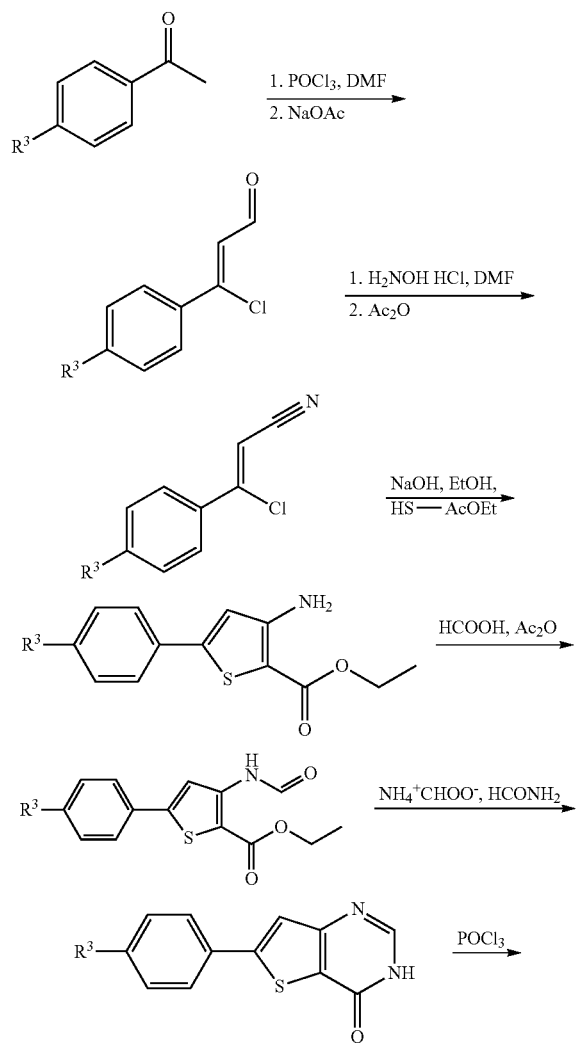

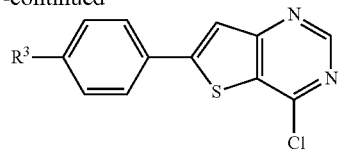

in which $R^3$ is the same as described above, preferably MeO (methoxy).

Further, a starting material of the general formula (6b):

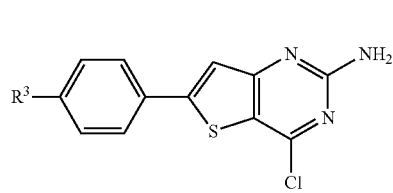

Formula (6b)

useful for the above method may e.g. be prepared by the following reaction sequence, wherein the individual steps are according to references [1], [3] and [17-22]:

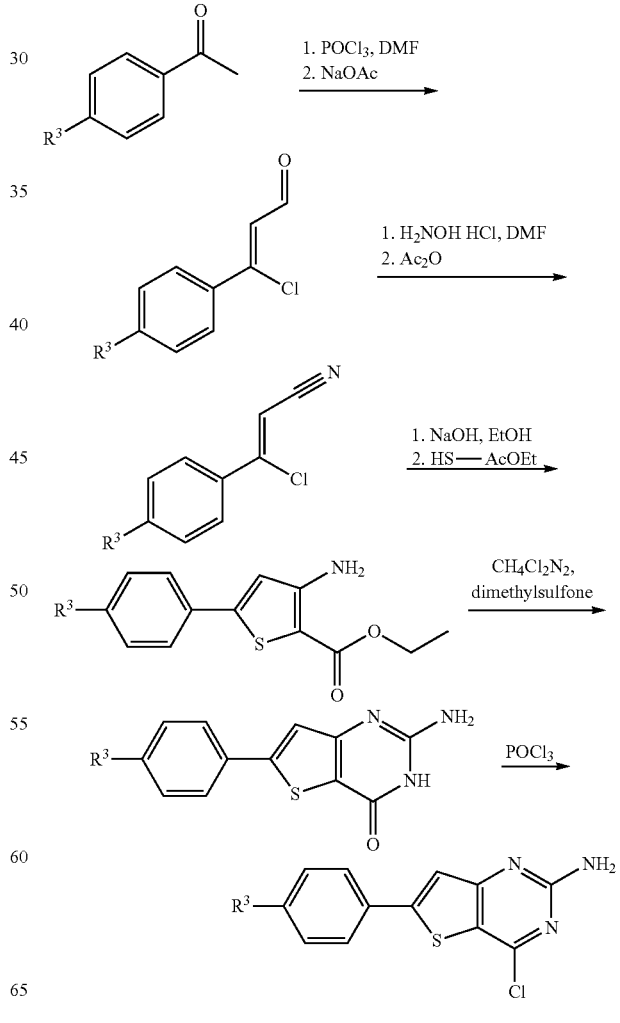

in which R³ is the same as described above, preferably MeO (methoxy).

Further, a starting material of the general formula (6c):

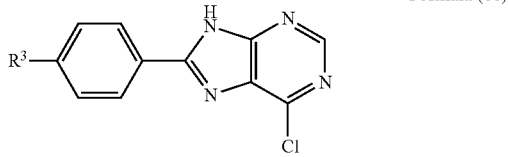

Formula (6c)

useful for the above method may e.g. be prepared by the following reaction sequence, wherein the individual steps are according to reference [24]:

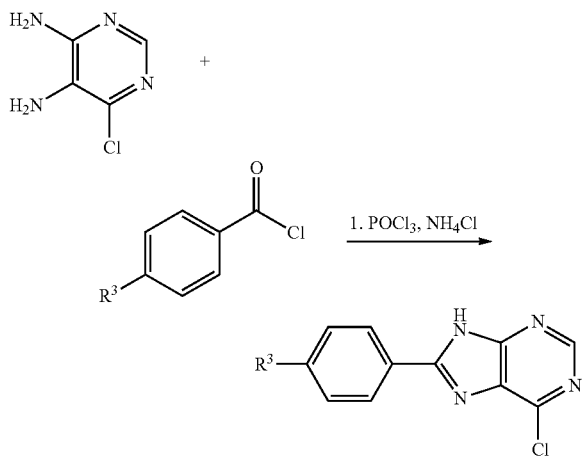

in which R³ is the same as described above, preferably MeO (methoxy).

Further, a starting material of the general formula (7):

Formula (7)

useful for the above method may be prepared by the following reaction according to references [6], [7] and [8]:

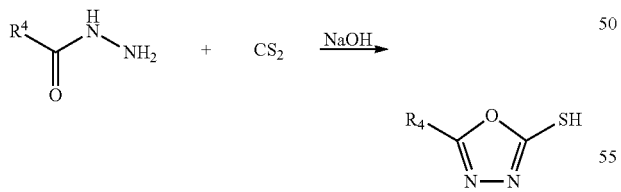

in which R⁴ is the same as described above, e.g. a benzyl group.

The present invention will be further illustrated in the following examples without being limited thereto.

EXAMPLES

General

Starting materials, reagents and solvents were mainly purchased from Acros Organics (Geel, Belgium), Sigma Aldrich (St. Louis, Mo., USA) and Alfa Aesar (Ward Hill, Mass., USA). 4-Chloro-6-(4-fluorophenyl)thieno[3,2-d]pyrimidine, 6-(4-chlorophenyl)-thieno[3,2-d]pyrimidine-4-thiol and 6-(4-fluorophenyl)thieno[3,2-d]pyrimidine-4-thiol were purchased from Enamine Ltd. (Kiev, Ukraine). Melting points were determined in open-glass capillaries on an electric variable heater (Electrothermal IA 9100). FT-IR absorption spectra were recorded on a Thermo Nicolet FT-IR 200 spectrometer using KBr pellets. $^1$H-NMR and $^{13}$C-NMR spectra were recorded on a Bruker Avance DRX-400 ($^1$H-NMR: 400.1 MHz, $^{13}$C-NMR: 100.6 MHz) and a Bruker Avance II-600 ($^1$H-NMR: 600.1 MHz, $^{13}$C-NMR: 150.9 MHz), respectively, using DMSO-$d_6$, CDCl$_3$ and acetone-$d_6$, respectively, as solvents (NMR laboratories of the Chemical Institutes of the Technische Universität Braunschweig). Chemical shifts are reported as parts per million (ppm) downfield from TMS used as an internal standard. The elemental analysis was recorded on a CE Instruments FlashEA® 1112 Elemental Analyzer. The reactions were monitored by TLC (Macherey-Nagel Polygram SIL G/UV254). HPLC experiments were performed on a Merck Hitachi LaChrom Elite system (pump: L-2130, DAD detector: L-2450; autosampler: L-2200; column: Merck LiChroCART 125-4, LiChrospher 100 RP-18 (5 Å); elution rate 1.000 mL/min; detection wavelength: 254 nm and 280 nm; overall run time: 15 min unless otherwise described); $t_{MS}$=total retention time, $t_M$=dead time; eluents: mixtures of acetonitrile and double distilled water or triethylammonium sulphate buffer (pH 2.3); buffer preparation: 20 mL triethylamine and 0.242 g sodium hydroxide dissolved in 1000 mL double distilled water and adjusted to pH 2.3 with concentrated sulphuric acid. Gradient HPLC was performed on a Merck Hitachi LaChrom Elite system (pump: L-2130, UV detector: L-2400; autosampler: L-2200; column: Merck LiChroCART 125-4, LiChrospher 100 RP-18 (5 Å); elution rate 1.000 mL/min; detection wavelength: 254 nm unless otherwise described; overall run time: 25 min unless otherwise described, the eluents were mixed on-line). The gradient elution conditions were as followed. Method 1: 0→10.0 min: acetonitrile/water 10/90→70/30; 10.0→10.5 min: acetonitrile/water 70/30→90/10; 10.5→16.5 min: acetonitrile/water 90/10. Method 2: 0→10.0 min: acetonitrile/water 10/90→70/30; 10.0→13.0 min: acetonitrile/water 70/30→90/10; 13.0→20.0 min: acetonitrile/water 90/10. $t_{MS}$=total retention time, $t_M$=dead time; eluents: mixtures of acetonitrile and double distilled water. The mass spectra were recorded on a Thermofinnigan MAT95XL (Department of mass spectrometry of the Chemical Institutes of the Technische Universität Braunschweig).

Syntheses of Compounds

3-Chloro-3-(4-methoxyphenyl)acrylaldehyde:[1]

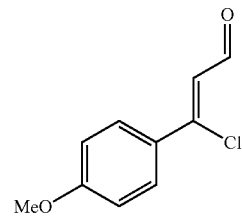 [SMILES: COc1ccc(/C(Cl)=C/C=O)cc1]

Experimental procedure taken from Romagnoli et al.[1]

Phosphoryl chloride (3.36 g, 2.00 mL, 21.9 mmol) was added dropwise to an ice-cooled stirred solution of N,N-dimethylformamide (10 mL). The solution was stirred for further 30 minutes. 4'-Methoxyacetophenone (0.751 g, 5.00 mmol) was added portionwise to the DMF-POCl₃ complex forming a yellow solution. Subsequently, the batch was heated at 70° C. for five hours. After cooling to room temperature, an aqueous, ice-cooled, saturated solution of sodium acetate (50 mL) was added. The resulting suspension was extracted with ethyl acetate (3×20 mL). The organic layer was washed with lithium chloride (5%, 20 mL), dried over anhydrous Na₂SO₄ and concentrated in vacuo. The yellow powder (Yield: 80.9%) was used without any further purification.

Mp=63-65° C. (58-60° C.[1])

¹H-NMR (DMSO-d₆, 400 MHz): 3.85 (s, 3H, CH₃), 6.92 (d, J=6.76, 2H, =CH—CHO), 7.06-7.09 (m, 2H, ArH), 7.88-7.92 (m, 2H, ArH), 10.10 (d, J=6.78, 1H, CHO).

3-Chloro-3-(4-methoxyphenyl)acrylonitrile:[2]

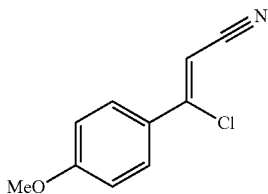 [SMILES: COc1ccc(/C(Cl)=C/C#N)cc1]

Experimental procedure taken from Romagnoli et al.[2]

3-Chloro-3-(4-methoxyphenyl)acrylaldehyde (0.750 g, 3.81 mmol) was dissolved in N,N-dimethylformamide (15 mL) in a nitrogen atmosphere. The solution was heated for six hours at 60° C. after addition of hydroxylamine hydrochloride (0.348 g, 5.00 mmol). Addition of ice-cooled water resulted in a colourless suspension. The product was extracted with ethyl acetate (3×50 mL). The organic layer was washed with water (20 mL), dried over anhydrous Na₂SO₄ and concentrated in vacuo. Acetic anhydride (30 mL) was added to the remaining oil and the solution was stirred for 18 hours at 130° C. to convert the aldoxime into desired nitrile. The dehydration agent was evaporated in vacuo. The complete batch of the remaining residue was used without any further purification for the following synthesis.

Mp=103-105° C. (88-90° C.[16])

¹H-NMR (DMSO-d₆, 400 MHz): 3.84 (s, 3H, CH₃), 6.81 (s, 1H, =CH—C), 7.06-7.09 (m, 2, ArH), 7.78-7.80 (m, 2H, ArH).

Ethyl 3-amino-5-(4-methoxyphenyl)thiophene-2-carboxylate:[3]

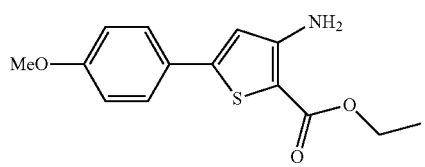 [SMILES: CCOC(=O)c1sc(-c2ccc(OC)cc2)cc1N]

Experimental procedure taken from Hartmann et al.[3]

Ethyl 2-mercaptoacetate (0.601 g, 0.551 μL, 5.00 mmol) was added to an equimolar solution of sodium hydroxide in ethanol (10 mL). The solution was stirred at room temperature for 15 min. Subsequently, the batch of R-chloro cinnamic acid nitrile as produced by the method described above was added and the resulting solution was refluxed for two hours. After cooling to room temperature, ice-cooled water (30 mL) was added and the precipitate filtered. The product (Yield: 65.4%, calculated over two steps from 3-chloro-3-(4-methoxyphenyl)acrylaldehyde) was recrystallized from n-butanol.

Mp=123-125° C. (119-120° C.[3])

¹H-NMR (DMSO-d₆, 400 MHz): 1.26 (t, J=7.09 Hz, 3H, CH₃), 3.80 (s, 3H, CH₃), 4.20 (q, J=7.09 Hz, 2H, CH₂), 6.55 (s, 2H, NH₂), 6.87 (s, 1H, ArH), 6.98-7.02 (m, 2H, ArH), 7.56-7.59 (m, 2H, ArH).

Ethyl 3-formamido-5-(4-methoxyphenyl)thiophene-2-carboxylate

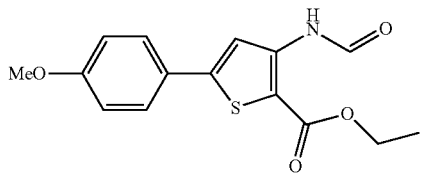 [SMILES: CCOC(=O)c1sc(-c2ccc(OC)cc2)cc1NC=O]

Experimental procedure taken from Thrash et al.[4]

Formic acid (4 mL) was added to ice-cooled acetic anhydride (6 mL). Ethyl 3-amino-5-(4-methoxyphenyl)thiophene-2-carboxylate (1.39 g, 5.01 mmol) was added portionwise and then stirred for four hours at room temperature. Consecutively, the reaction batch was poured on an ice-cooled solution of 5.00 g Na₂CO₃ in 20 mL water. The resulting brown oil was extracted with ethyl acetate (3×20 mL). The organic layer was washed with lithium chloride (5%, 20 mL), dried over anhydrous Na₂SO₄ and concentrated in vacuo to yield 50% of a crude product which was used without any further purification.

Mp=121-123° C.

¹H-NMR (DMSO-d₆, 400 MHz): 1.30-1.34 (t, J=7.09 Hz, 3H, CH₃), 3.81 (s, 3H, CH₃), 4.30-4.35 (q, J=7.08 Hz, 2H, CH₂), 7.02-7.04 (m, 2H, ArH), 7.64-7.67 (m, 2H, ArH), 8.21 (s, 1H, ArH), 8.44 (s, 1H, CHO), 10.41 (s, 1H, NH).

6-(4-Methoxyphenyl)thieno[3,2-d]pyrimidin-4(3H)-one:[15]

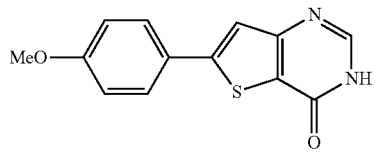 [SMILES: COc1ccc(-c2cc3nc[nH]c(=O)c3s2)cc1]

Experimental procedure taken from Thrash et al.[4]

Ethyl 3-formamido-5-(4-methoxyphenyl)thiophene-2-carboxylate (1.00 g, 3.27 mmol), ammonium formate (2.60 g, 5.00 mmol) and formamide (4 mL) were heated for six hours at 160° C. in a nitrogen atmosphere. The solution was cooled to room temperature and the precipitates were filtered, washed with acetone and dried over phosphorus pentoxide (Yield: 50.0%).

Mp=288-290° C.

¹H-NMR (DMSO-d₆, 400 MHz): 3.83 (s, 3H, CH₃), 7.04-7.07 (m, 2H, ArH), 7.71 (s, 1H, ArH), 7.78-7.82 (m, 2H, ArH), 8.15 (s, 1H, ArH), 12.40 (s, 1H, NH).

4-Chloro-6-(4-methoxyphenyl)thieno[3,2-d]pyrimidine

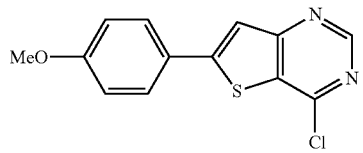 [SMILES: COc1ccc(-c2cc3ncnc(Cl)c3s2)cc1]

Experimental procedure taken from Thrash et al.[4]

6-(4-Methoxyphenyl)thieno[3,2-d]pyrimidin-4(3H)-one (0.500 g, 1.94 mmol) in phosphoryl chloride (5 mL) was refluxed for two hours in a nitrogen atmosphere. Subsequently, the solution was cooled to room temperature and carefully added to an aqueous saturated sodium carbonate solution (5.40 g $Na_2CO_3$/25 mL). The aqueous solution was extracted with ethyl acetate (3×25 mL). The organic layer was then washed with brine and dried over anhydrous $Na_2SO_4$. The solvent was evaporated in vacuo (Yield: 25.7%).

Mp=174-176° C.

$^1$H-NMR (DMSO-$d_6$, 400 MHz): 3.85 (s, 1H, $CH_3$), 7.09-7.12 (m, 2H, ArH), 7.93-7.95 (m, 2H, ArH), 8.10 (s, 1H, ArH), 8.98 (s, 1H, ArH).

$^{13}$C-NMR (DMSO-$d_6$): δ6.0 (prim. C); 115.4 (2C), 119.2, 129.0 (2C), 155.2 (tert. C); 124.6, 129.3, 153.1, 155.1, 161.9, 163.4 (quat. C).

Chloroformamidine Hydrochloride

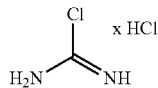

Experimental procedure taken from Henderson et al. [22].

Cyanamide (1.00 g, 23.8 mmol) was dissolved in acetic anhydride (75.0 mL) and hydrogen chloride gas was passed through the ice-cooled solution via a wide glass tube for 2.5 h forming a white precipitate. The product was collected by filtration, washed well with acetic anhydride and petroleum ether and dried in vacuo to yield a white solid (2.62 g, 95.9%).

Mp=175-177° C.

$^1$H-NMR (DMSO-$d_6$, 400 MHz): 7.09 (s, 2H, $NH_2$), 10.71 (s, 1H, NH).

2-Amino-6-(4-methoxyphenyl)thieno[3,2-d]pyrimidin-4(3H)-one

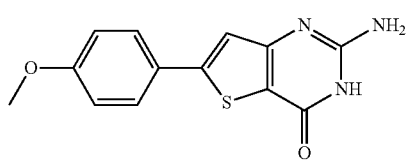 [SMILES: COc1ccc(-c2cc3nc(N)[nH]c(=O)c3s2)cc1]

Experimental procedure taken from Abdillahi et al. [17], Savall et al. [18] and Edwards et al. [19].

Ethyl 3-amino-5-(4-methoxyphenyl)thiophene-2-carboxylate (0.832 g, 3.00 mmol) and chloroformamidine hydrochloride (0.517 mg, 4.50 mmol) were mixed with dimethylsulfone (0.847 g, 9.00 mmol) and heated at 140-150° C. for one hour. Subsequently, the viscous solution was cooled to room temperature and mixed with an aqueous ice-cooled solution of sodium hydroxide (0.400 g, 10.0 mL). The aqueous solution was extracted with ethyl acetate (3×25 mL). The aqueous solution was neutralized with diluted hydrochloric acid (5% v/v) until precipitation started. The precipitates were filtered of and recrystallized from ethanol to yield brown powder (Yield: 36.0%).

Mp=326-328° C.

$^1$H-NMR (DMSO-$d_6$, 400 MHz): 3.81 (s, 3H, $CH_3$), 6.90 (s, 2H, $NH_2$), 7.01-7.04 (m, 2H, ArH), 7.25 (s, 1H, ArH), 7.68-7.71 (m, 2H, ArH).

$^{13}$C-NMR (DMSO-$d_6$, 100 MHz): 56.1 (prim. C); 114.6 (2C), 118.3, 127.4 (2C) (tert. C); 110.5, 125.8, 149.7, 155.5, 158.9, 160.1, 174.4 (quart. C).

4-Chloro-6-(4-methoxyphenyl)thieno[3,2-d]pyrimidin-2-amine

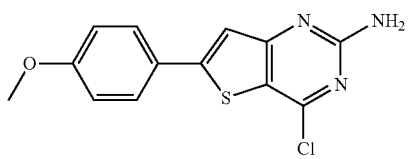 [SMILES: COc1ccc(-c2cc3nc(N)nc(Cl)c3s2)cc1]

Experimental procedure taken from Ife et al. [20] and Jang et al. [21].

2-Amino-6-(4-methoxyphenyl)thieno[3,2-d]pyrimidin-4(3H)-one (0.322 g, 1.18 mmol) and N,N-dimethylaniline (1.00 mL) in phosphoryl chloride (10 mL) were refluxed for 90 minutes. Subsequently, the volatiles were removed in vacuo and ice-cooled water (50 mL) was added. Upon addition of triethylamine (5 mL), the solution was extracted with dichloromethane (3×25 mL). The combined organic layers were evaporated in vacuo and recrystallized from dichloromethane to yield brown powder (Yield: 15.6%).

Mp=230-231° C.

IR (KBr): 3469 $cm^{-1}$, 3304 $cm^{-1}$, 3184 $cm^{-1}$.

$^1$H-NMR (DMSO-$d_6$, 600 MHz): 3.83 (s, 3H, $CH_3$), 7.00 (s, 2H, $NH_2$), 7.06-7.08 (m, 2H, ArH), 7.58 (s, 1H, ArH), 7.82-7.84 (m, 2H, ArH).

$^1$H-NMR ($CDCl_3$-$d_1$, 400 MHz): 3.88 (s, 3H, $CH_3$), 5.70 (s, 2H, $NH_2$), 6.97-7.01 (m, 2H, ArH), 7.25 (s, 1H, ArH), 7.66-7.69 (m, 2H, ArH).

$^{13}$C-NMR (DMSO-$d_6$, 150.9 MHz): 56.0 (prim. C); 115.2 (2C), 117.2, 128.5 (2C) (tert. C); 118.1, 125.2, 153.1, 154.0, 161.4, 162.3, 165.5 (quart. C).

$^{13}$C-NMR ($CDCl_3$-$d_1$, 100 MHz): 55.5 (prim. C); 114.6 (2C), 116.4, 128.1 (2C) (tert. C); 119.9, 125.3, 154.3, 156.0, 160.8, 161.4, 163.7 (quart. C).

HRMS/ESI (+): calcd. $[C_{13}H_{11}ClN_3OS]^+$=292.03039; found 292.03075 $[M+H]^+$.

HPLC: 97.9% at 254 nm; 95.6% at 280 nm; $t_{MS}$=3.13 min, (ACN/$H_2O$; 70:30); $\lambda_{max}$: 328 nm.

6-Chloro-8-phenyl-9H-purine

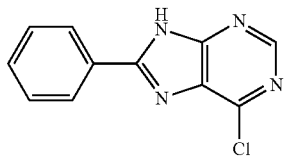 [SMILES: Clc1ncnc2[nH]c(-c3ccccc3)nc12]

Experimental procedure taken from Ibrahim et al. [24].

A mixture of 6-chloro-4,5-diaminopyrimidine (1.4 mmol) and ammonium chloride (8.40 mmol) was suspended in POCl$_3$ (10.0 mL). After addition of benzoyl chloride (7.00 mmol) the reaction batch was heated for 24 hours at 100° C. After cooling to room temperature and pouring into ice/water, the mixture was neutralized with ammonia solution (25% v/v) to pH 7-8. The obtained solid was filtered off and washed with water. The product was used without any further purification.

Mp=254-255° C.

$^1$H-NMR (DMSO-d$_6$, 400 MHz): δ (ppm)=7.62 (m, 3H, ArH), 8.29 (m, 2H, ArH), 8.73 (s, 1H, ArH), 14.4 (s, 1H, NH).

$^{13}$C-NMR (DMSO-d$_6$, 100 MHz): d (ppm)=127.3, 128.4 (2C), 131.6 (2C), 151.4 (tert. C), 129.2 (quart. C).

1,3,4-Oxadiazole-2-thioles and 1,3,4-oxadiazole-2(3H)-thiones were either purchased from commercial vendors or synthesized as described below.

Syntheses of 1,3,4-Oxadiazole Derivatives

Method A:

With reference to Manjunatha et al., the 1,3,4-oxadiazole derivatives were synthesized as described below:[6]

The appropriate hydrazide (10.0 mmol) was dissolved in ethanol 96% (30 mL) with addition of sodium hydroxide (0.400 g, 10.0 mmol). After the addition of carbon disulfide 0.776 g, 10.2 mmol) the reaction batch was refluxed for four hours. The mixture was cooled to room temperature. Addition of 1 M hydrochloric acid (10.0 mL) led to precipitation. The precipitates were filtered, washed with water and recrystallized from ethanol.

Method B:

With reference to Farghaly et al., the 1,3,4-oxadiazole derivatives were synthesized as described below:[7]

The appropriate hydrazide (10.0 mmol) was dissolved in pyridine (40 mL) with addition of carbon disulfide (0.776 g, 10.2 mmol). The reaction batch was refluxed for six hours. The mixture was cooled to room temperature. The solvent was evaporated in vacuo and the residue was recrystallized from ethanol.

Method C:

With reference to Jansen et al. the 1,3,4-oxadiazole derivatives were synthesized as described below:[8]

The appropriate ester (1.00 mmol) was dissolved in ethanol (10 mL) with addition of hydrazine hydrate (0.320 g, 10.0 mmol). The reaction batch was refluxed for three hours. The mixture was cooled to room temperature and the solvent was evaporated in vacuo. The residue was further processed as described in method B without prior purification.

Method D:

The appropriate hydrazide (1.00 mmol) was dissolved in methanol (20 mL) with addition of N,N-diisopropylethylamine (0.194 g, 1.5 mmol) and carbon disulfide (2.52 g, 33.1 mmol). The reaction batch was refluxed for three hours. The mixture was cooled to room temperature. The solvent was evaporated in vacuo and the residue was recrystallized from ethanol.

5-Benzyl-1,3,4-oxadiazole-2-thiol:[10]

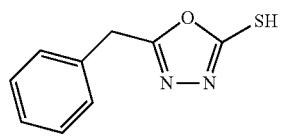 [SMILES: Sc1nnc(Cc2ccccc2)o1]

The compound was synthesized as described in method A; light yellow powder (Yield: 93%).

Mp=125-127° C. (129-130° C.[10])

$^1$H-NMR (DMSO-d$_6$, 400 MHz): 4.14 (s, 2H, CH$_2$), 7.28-7.41 (m, 5H, ArH), 14.12 (s, br, 1H, SH).

$^{13}$C-NMR (DMSO-d$_6$, 100 MHz): 31.0 (sec. C); 127.4, 128.8 (2C), 129.0 (2C) (tert. C); 133.5, 163.0, 177.8 (quat. C).

MS (EI): m/z (%)=192 [M]$^{+\bullet}$ (69).

5-(Pyridin-4-yl)-1,3,4-oxadiazole-2-thiol:[11]

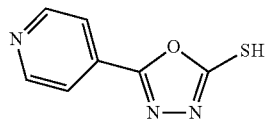 [SMILES: Sc1nnc(-c2ccncc2)o1]

The compound was synthesized as described in method B; orange powder (Yield: 88%).

Mp=276° C. (272° C.[11])

$^1$H-NMR (DMSO-d$_6$, 400 MHz): 7.82 (dd, J=1.65, 4.49, 2H, ArH)), 8.82 (d, J=4.69, 2H, ArH).

$^{13}$C-NMR (DMSO-d$_6$, 100 MHz): 119.6 (2C), 150.8 (2C) (tert. C); 129.8, 158.8, 177.8 (quat. C).

MS (EI): m/z (%)=179 [M]$^{+\bullet}$ (100).

Anal. calcd. for C$_7$H$_5$N$_3$OS: C, 46.92; H, 2.81; N, 23.45. Found: C, 47.18; H, 2.60; N, 23.08.

5-[(Dimethylamino)methyl]-1,3,4-oxadiazole-2-thiol:[8]

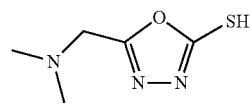

The compound was synthesized as described in method C (Yield: 65%).

Mp=225° C. (119° C.[8])

$^1$H-NMR (DMSO-d$_6$, 400 MHz): 2.33 (s, 6H, CH$_3$), 3.73 (s, 2H, CH$_2$).

$^{13}$C-NMR (DMSO-d$_6$, 100 MHz): 44.0 (prim. C); 51.8 (sec. C); 160.0, 175.5 (quat. C).

MS (EI): m/z (%)=159 [M]$^{+\bullet}$ (42).

5-(Morpholinomethyl)-1,3,4-oxadiazole-2-thiol:[12]

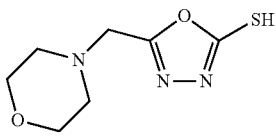 [SMILES: Sc1nnc(CN2CCOCC2)o1]

The compound was synthesized as described in method C; white powder (Yield: 88%).
$^1$H-NMR (DMSO-d$_6$, 400 MHz): 2.46-2.49 (m, 4H, CH$_2$), 3.57-3.59 (m, 4H, CH$_2$), 3.56 (s, 2H, CH$_2$).
$^{13}$C-NMR (DMSO-d$_6$, 100 MHz): 51.5, 52.4 (2C), 66.0 (2C) (sec. C); 160.6, 178.0 (quat. C).

5-[4-(Trifluoromethyl)phenyl]-1,3,4-oxadiazole-2-thiol:[13]

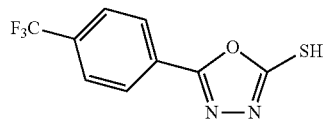

The compound was synthesized as described in method A, (Yield: 83%).
MS (EI): m/z (%)=246 [M]$^{+\bullet}$ (100).
$^1$H-NMR (DMSO-d$_6$, 400 MHz): 7.85-8.04 (m, 4H, ArH).

5-(3-Methoxybenzyl)-1,3,4-oxadiazole-2(3H)-thione:[14]

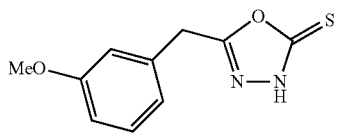 [SMILES: COc1cccc(Cc2n[nH]c(=S)o2)c1]

The compound was synthesized as described in method D, (Yield: 86.4%).
Mp=146-148° C.
$^1$H-NMR (DMSO-d$_6$, 400 MHz): 3.52 (s, 2H, CH$_2$), 3.81 (s, 3H, CH$_3$), 6.84-6.93 (m, 3H, ArH), 7.27 (t, J=7.84, 1H, ArH), 8.30 (s, 1H, NH).

5-(tert-Butyl)-1,3,4-oxadiazole-2-thiol:[15]

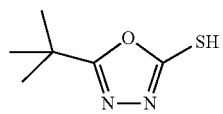

The compound was synthesized as described in method D, (Yield: 76.0%).
$^1$H-NMR (DMSO-d$_6$, 400 MHz): 1.30 (s, 9H, CH$_3$).
$^{13}$C-NMR (DMSO-d$_6$, 100 MHz): 26.9 (3C) (tert. C); 32.1, 169.8, 177.8 (quat. C).

5-(2,4-Dichlorophenyl)-1,3,4-oxadiazole-2-thiol

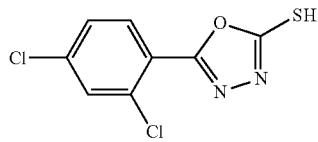 [SMILES: Sc1nnc(-c2ccc(Cl)cc2Cl)o1]

The compound was synthesized as described in method A, (Yield: 85.2%).[25]
Mp=169-171° C.
IR (KBr): 3015 cm$^{-1}$, 2887 cm$^{-1}$, 2731 cm$^{-1}$, 2558 cm$^{-1}$.
$^1$H-NMR (DMSO-d$_6$, 400 MHz): 7.65-7.67 (m, 1H, ArH), 7.92-7.94 (m, 2H, ArH), 14.92 (brs, 1H).
$^{13}$C-NMR (DMSO-d$_6$, 100 MHz): 128.2, 130.8, 132.0 (tert. C); 120.4, 132.6, 137.3, 157.7, 177.3 (quart. C).
MS (EI): m/z (%)=246 [M]$^{+\bullet}$ (86).

5-(Furan-2-yl)-1,3,4-oxadiazole-2-thiol

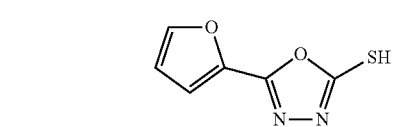

The compound was synthesized as described in method A and recrystallized from methanol; white solid (Yield: 36%).[23]
Mp=172° C.
$^1$H-NMR (DMSO-d$_6$, 400 MHz): δ (ppm)=6.80 (dd, 1H; J=1.78/3.60 Hz, ArH), 7.35 (dd, 1H, J=0.77/3.61 Hz, ArH), 8.05 (dd, 1H, J=0.77/1.78 Hz, ArH), 14.8 (s, 1H, SH).
$^{13}$C-NMR (DMSO-d$_6$, 100 MHz): 112.6, 115.0, 147.2 (tert. C), 137.5, 153.5, 176.7 (quart. C).

Synthesis of
6-Aryl-4-arylthiothieno[3,2-d]pyrimidine
Derivatives

Method E:
The appropriate thiol or thione (0.400 mmol) was dissolved in n-butanol (10 mL) with added base N,N-diisopropylmethylamine (0.694 g, 0.602 mmol, 0.0920 mL). After addition of the thieno pyrimidine component (0.400 mmol) the suspension was heated at 100° C. for six hours. After evaporation of the solvent the product was obtained by recrystallization from toluene.

Method F:
The appropriate thiol (0.500 mmol) was suspended in acetonitrile (10 mL) with added potassium carbonate (0.0829 g, 0.600 mmol). After addition of the thieno pyrimidine component (0.500 mmol) the suspension was heated at 90° C. for 12 hours. The product was obtained after evaporation of the solvent and recrystallization from toluene.

Method G:
The appropriate thiol (0.400 mmol) was dissolved in n-butanol (10 mL) with added base N,N-diisopropylethylamine (0.103 g, 0.800 mmol, 0.136 mL). After addition of the thieno pyrimidine component (0.400 mmol) the suspension was heated at 100° C. for six hours. The product was obtained after evaporation of the solvent and recrystallization from toluene.

Method H:

The thieno pyrimidine (0.138 g, 0.500 mmol) component was dissolved in ethanol (5 mL) with added sodium hydroxide (0.0200 g, 0.500 mmol). The suspension was heated at 100° C. for six hours. The product was obtained after evaporation of the solvent and recrystallization from toluene.

Method I:

The appropriate thiol (0.360 mmol) was dissolved in n-butanol (5.00 mL) with added base triethylamine (0.0506 g, 0.500 mmol, 0.0690 mL). After addition of the thieno[3,2-d]pyrimidine component (0.3600 mmol) the suspension was heated at 100° C. for 20 hours. After evaporation of the solvent the product was obtained by recrystallization from ethanol.

Method J:

In a thick-walled sealed microwave vessel the thieno[3,2-d]pyrimidine component (0.500 mmol) and the appropriate thiol (1.00 mmol) were dissolved in N,N-dimethylformamide (2.00 mL) with addition of triethylamine (1.00 mmol, 0.101 g).

The reaction mixture was heated in a synthesis microwave for 20 minutes at 120° C., 100 W, ramp time 5 min, maximum pressure 150 Psi. Upon addition of ice-cooled water (2.00 mL) the target compound precipitated and was filtered off, washed with water and the residue recrystallized from n-butanol.

Method K:

The appropriate 1,3,4-oxadiazole-2-thiol (0.350 mmol) was dissolved in n-butanol (10 mL) with added base N,N-diisopropylethylamine (0.350 mmol). After addition of 6-chloro-8-phenyl-9H-purine (0.350 mmol) the suspension was heated at 100° C. for four hours. After cooling to room temperature, the obtained solid was filtered off, washed with water and recrystallized from n-butanol.

Method L:

The appropriate 1,3,4-oxadiazole-2-thiol-derivative (0.800 mmol) and 6-chloro-8-phenyl-9H-purine (0.400 mmol) were dissolved in DMF (1.00 mL) under addition of N,N-diisopropylethylamine (0.800 mmol). The reaction mixture was heated in a synthesis microwave for 20 minutes at 120° C., 100 W, ramp time 5 min, maximum pressure 150 Psi. Upon addition of ice-cooled water (2.00 mL) the target compound precipitated and was filtered off, washed with water and the residue recrystallized from ethanol.

2-{[6-(4-Fluorophenyl)thieno[3,2-d]pyrimidin-4-yl]thio}-5-phenyl-1,3,4-oxadiazole (8a)

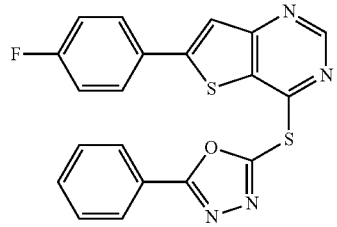

8a

Compound 8a was synthesized as described in method G; light yellow powder (Yield: 86.0%).

Mp=223° C.

IR (KBr): 3086 cm$^{-1}$, 3057 cm$^{-1}$, 3043 cm$^{-1}$ (C—H, aromat.).

$^1$H-NMR (CDCl$_3$, 400 MHz): 7.17-7.23 (m, 2H, ArH), 7.51-7.61 (m, 3H, ArH), 7.67 (s, 1H, ArH), 7.73-7.75 (m, 2H, ArH), 8.10-8.12 (m, 2H, ArH), 8.91 (s, 1H, ArH).

$^{13}$C-NMR (CDCl$_3$, 100 MHz): 116.6, 116.8, 119.7, 127.3 (2C), 129.0 (2C), 129.2 (2C), 132.5, 154.6 (tert. C); 123.4, 128.6, 153.1, 156.2, 157.5, 161.6, 162.9, 165.4, 168.6 (quat. C).

Anal. calcd. for C$_{20}$H$_{11}$FN$_4$OS$_2$: C, 59.10; H, 2.73; N, 13.78.

Found: C, 58.88; H, 2.40; N, 13.45.

MS (EI): m/z (%)=406 [M]$^{+\bullet}$ (4).

HPLC: 99.3% at 254 nm; 99.4% at 280 nm; t$_{MS}$=5.47 min, t$_M$ (DMSO)=1.05 min (ACN/H$_2$O; 70:30); λ$_{max}$: 260 nm and 317 nm.

2-{[6-(4-Fluorophenyl)thieno[3,2-d]pyrimidin-4-yl]thio}-5-(pyridin-4-yl)-1,3,4-oxadiazole (8b)

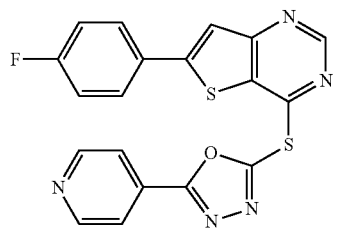

8b

Compound 8b was synthesized as described in method G; light yellow powder (Yield: 85.0%).

Mp=232° C.

IR (KBr): 3428 cm$^{-1}$, 3060 cm$^{-1}$ (C—H, aromat.).

$^1$H-NMR (DMSO-d$_6$, 400 MHz): 7.39-7.45 (m, 2H, ArH), 8.0-8.01 (m, 2H, ArH), 8.05-8.09 (m, 2H, ArH), 8.22 (s, 1H, ArH), 8.86-8.88 (m, 2H, ArH), 8.98 (s, 1H, ArH).

MS (EI): m/z (%)=407 [M]$^{+\bullet}$ (7).

HRMS (EI): m/z [M]$^{+\bullet}$ calcd. 407.03053, found 407.03059.

HPLC: 96.8% bei 254 nm; 95.8% at 280 nm; t$_{MS}$=3.63 min, t$_M$ (DMSO)=1.06 min (ACN/H$_2$O; 70:30); λ$_{max}$: 252 nm and 318 nm.

1-{5-[(6-{4-Fluorophenyl}thieno[3,2-d]pyrimidin-4-yl)thio]-1,3,4-oxadiazol-2-yl}-N,N-dimethylmethanamine (8c)

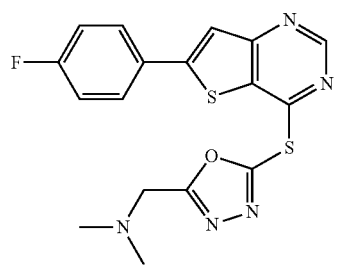

8c

Compound 8c was synthesized as described in method G; light yellow powder (Yield: 65.0%).

Mp=170-172° C.

IR (KBr): 3055 cm$^{-1}$, 3075 cm$^{-1}$ (C—H, aromat.); 2830 cm$^{-1}$, 2776 cm$^{-1}$ (CH$_2$N(CH$_3$)$_2$)).

¹H-NMR (CDCl₃, 400 MHz): 2.40 (s, 6H, CH₃), 3.89 (s, 2H, CH₂), 7.18-7.23 (m, 2H, ArH), 7.66 (s, 1H, ArH), 7.72-7.78 (m, 2H, ArH), 8.87 (s, 1H, ArH).
¹³C-NMR (CDCl₃, 100 MHz): 45.0 (prim. C); 53.1 (sec. C); 116.7 (2C), 119.6, 129.0 (2C), 154.5 (tert. C); 128.5, 128.7, 153.0, 157.3, 161.6, 163.3, 165.0, 168.0 (quat. C).
Anal. calcd. for C₁₇H₁₄FN₅OS: C, 52.70; H, 3.64; N, 18.08.
Found: C, 52.63; H, 3.45; N, 17.83.
MS (EI): m/z (%)=386 [M]⁺• (1), 344 (100).
HPLC: 95.1% at 254 nm; 96.4% at 280 nm; $t_{MS}$=2.57 min, (ACN/buffer; 40:60); $\lambda_{max}$: 243 nm and 321 nm.

4-{[5-({6-[4-Fluorophenyl]thieno[3,2-d]pyrimidin-4-yl}thio)-1,3,4-oxadiazol-2-yl]methyl}morpholine (8d)

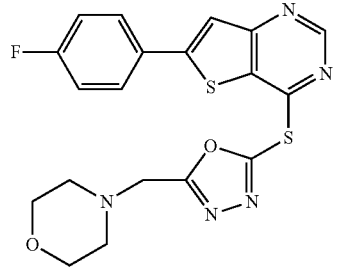

8d

Compound 8d was synthesized as described in method G; light yellow powder (Yield: 70.0%).
Mp=170-172° C.
IR (KBr): 3058 cm⁻¹, 2967 cm⁻¹ (C—H, aromat.); 2854 cm⁻¹, 2932 cm⁻¹ (CH₂N(CH₂)₂)).
¹H-NMR (acetone-d₆, 400 MHz): 2.56-2.58 (m, 4H, CH₂), 3.59-3.61 (m, 4H, CH₂), 3.96 (s, 2H, CH₂), 7.34-7.40 (m, 2H, ArH), 7.97 (s, 1H, ArH), 8.02-8.06 (m, 2H, ArH), 8.89 (s, 1H, ArH).
¹³C-NMR (acetone-d₆, 100 MHz): 52.7, 53.6 (2C), 67.3 (2C) (sec. C); 117.4 (2C), 121.0, 130.2 (2C), 155.4 (tert. C); 129.1, 153.7, 157.7, 158.3, 162.9, 164.2, 165.8, 168.8 (quat. C).
HRMS (EI): m/z [M-C₄H₇NO]+⁺• calcd. 344.01963, found 344.01989.
HPLC: 97.8% at 254 nm; 97.3% at 280 nm; $t_{MS}$=5.04 min (ACN/buffer; 50:50); $\lambda_{max}$: 248 nm and 318 nm.

2-{[6-(4-Fluorophenyl)thieno[3,2-d]pyrimidin-4-yl]thio}-5-[4-(trifluoromethyl)-phenyl]-1,3,4-oxadiazole (8e)

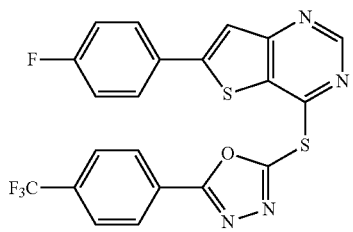

8e

Compound 8e was synthesized as described in method E; light yellow powder (Yield: 85.0%).
Mp=233-235° C.
IR (KBr): 3098 cm⁻¹ (C—H, aromat).

¹H-NMR (CDCl₃, 400 MHz): 7.20-7.23 (m, 2H, ArH), 7.68 (s, 1H, ArH), 7.75-7.78 (m, 2H, ArH), 7.80-7.82 (m, 2H, ArH), 8.24-8.25 (m, 2H, ArH), 8.90 (s, 1H, ArH).
¹³C-NMR (CDCl₃, 100 MHz): 116.6 (2C), 119.7, 126.3 (2C), 127.6 (2C), 129.0 (2C), 154.7 (tert. C); 128.5, 134.0, 134.2, 153.2, 157.0, 157.2, 161.7, 163.3, 165.0, 167.4 (quat. C).
MS (EI): m/z (%)=474 [M]⁺• (7).
HRMS (EI): m/z [M]⁺• calcd. 474.02267, found 474.02226.
HPLC: 98.2% at 254 nm; 98.8% at 280 nm; $t_{MS}$=7.22 min, $t_M$(DMSO)=1.04 min (ACN/H₂O; 70:30); $\lambda_{max}$: 256 nm and 318 nm.

2-{[6-(4-Fluorophenyl)thieno[3,2-d]pyrimidin-4-yl]thio}-5-(3-methoxybenzyl)-1,3,4-oxadiazole (8f)

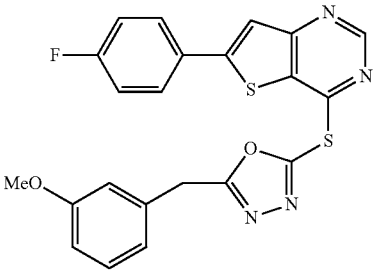

8f

Compound 8f was synthesized as described in method E; light brown powder (65.0%).
Mp=166-168° C.
IR (KBr): 3077 cm⁻¹, 3005 cm⁻¹ (C—H, aromat.); 2942 cm⁻¹ (C—H, aliphat.).
¹H-NMR (CDCl₃, 400 MHz): 3.77 (s, 3H, CH₃), 4.28 (s, 2H, CH₂), 6.79-6.90 (m, 3H, ArH), 7.17-7.21 (m, 2H, ArH), interference with 7.20 (m, 1H, ArH), 7.64 (s, 1H, ArH), 7.69-7.73 (m, 2H, ArH), 8.88 (s, 1H, ArH).
¹³C-NMR (CDCl₃, 100 MHz): 55.2 (prim. C); 32.1 (sec. C); 113.0, 114.6, 116.5, 116.7, 119.6, 121.1, 128.9, 129.0, 129.9, 154.5 (tert. C); 128.5, 128.7, 134.6, 153.0, 157.0, 157.4, 160.0, 161.6, 169.5 (quat. C).
HRMS (EI): m/z [M]⁺• calcd. 449.05367, found 449.05481.
HPLC: 96.8% at 254 nm; 98.9% at 280 nm; $t_{MS}$=6.96 min, $t_M$(DMSO)=1.02 min (ACN/H₂O; 60:40); $\lambda_{max}$: 246 nm and 318 nm.

2-(tert-Butyl)-5-{[6-(4-fluorophenyl)thieno[3,2-d]pyrimidin-4-yl]thio}-1,3,4-oxadiazole (8g)

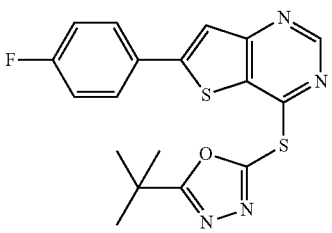

8g

Compound 8g was synthesized as described in method E; light yellow powder (Yield: 71.0%).
Mp=197-199° C.
IR (KBr): 3055 cm$^{-1}$ (C—H, aromat); 2976 cm$^{-1}$, 2935 cm$^{-1}$ (C—H, aliphat.).
$^1$H-NMR (DMSO-d$_6$, 600 MHz): 1.40 (s, 9H, CH$_3$), 4.28 (s, 2H, CH$_2$), 7.41-7.45 (m, 2H, ArH), 8.02-8.05 (m, 2H, ArH), 8.20 (s, 1H, ArH), 8.97 (s, 1H, ArH).
$^{13}$C-NMR (DMSO-d$_6$, 150.9 MHz): 27.5 (prim. C); 116.5, 116.6, 120.2, 129.2, 129.3, 154.4 (tert. C); 32.4, 127.5, 128.1, 152.2, 155.7, 157.3, 161.4, 176.8 (quat. C).
Anal. calcd. for C$_{18}$H$_{15}$FN$_4$OS$_2$: C, 55.94; H, 3.91; N, 14.50.
Found: C, 55.95; H, 3.81; N, 14.34.
MS (EI): m/z (%)=386 [M]$^{+\bullet}$ (3).
HPLC: 96.2% at 254 nm; 95.6% at 280 nm; t$_{MS}$=4.77 min, t$_M$(DMSO)=1.05 min (ACN/H$_2$O; 70:30); λ$_{max}$: 247 nm and 318 nm.

6-(4-Fluorophenyl)-4-{[4-(trifluoromethyl)phenyl]thio}thieno[3,2-d]pyrimidine (8h)

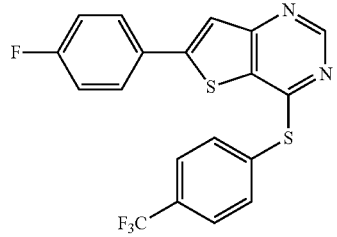

8h

Compound 8h was synthesized as described in method F; yellow powder (Yield: 80.0%).
Mp=172-175° C.
IR (KBr): 3048 cm$^{-1}$ (C—H, aromat.).
$^1$H-NMR (DMSO-d$_6$, 400 MHz): 7.38-7.44 (m, 2H, ArH), 7.88-7.95 (m, 4H, ArH), 8.01-8.06 (m, 2H, ArH), 8.14 (s, 1H, ArH), 8.90 (s, 1H, ArH).
$^{13}$C-NMR (DMSO-d$_6$, 100 MHz): 116.5 (2C), 120.2, 126.2 (2C), 129.1 (2C), 135.7 (2C), 154.4 (tert. C); 123.0, 124.7, 127.3, 128.4, 132.0, 151.1, 160.5, 162.4, 164.1 (quat. C).
Anal. calcd. for C$_{19}$H$_{10}$F$_4$N$_2$S$_2$: C, 56.15; H, 2.48; N, 6.89.
Found: C, 56.45; H, 2.44; N, 6.73.
MS (EI): m/z (%)=405 [M−H]$^{+\bullet}$ (100).
HPLC: 98.3% at 254 nm; 96.0% at 280 nm; t$_{MS}$=7.98 min, t$_M$(DMSO)=1.04 min (ACN/H$_2$O; 75:25); λ$_{max}$: 257 nm and 318 nm.

4-[(1H-imidazol-2-yl)thio]-6-(4-fluorophenyl)thieno[3,2-d]pyrimidine (8i)

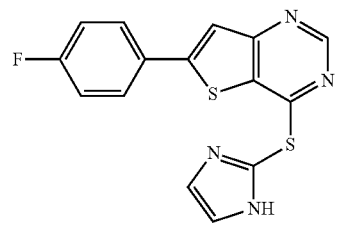

8i

Compound 8i was synthesized as described in method F; yellow powder (Yield: 80.0%).
Mp=204-206° C.
IR (KBr): 3108 cm$^{-1}$ (C—H, aromat.); 2914 cm$^{-1}$ (C—H, aliphat.).

$^1$H-NMR (DMSO-d$_6$, 600 MHz): 6.74 (d, J=1.7, 1H, ArH), 7.10 (d, J=1.8, 1H, ArH), 7.43-7.35 (m, 2H, ArH), 8.03-7.93 (m, with interference of 1H(s), 3H, ArH), 9.02 (s, 1H, ArH).
$^{13}$C-NMR (DMSO-d$_6$, 150.9 MHz): 116.3 (2C), 117.4, 118.4, 128.9 (2C), 153.8 (tert. C); 125.0, 152.5 153.8, 160.8, 162.2, 163.2, 163.9 (quat. C).
Anal. cald. for C$_{15}$H$_9$FN$_4$S$_2$: C, 54.86; H, 2.76; N, 17.06.
Found: C, 54.77; H, 2.70; N, 16.96.
MS (EI): m/z (%)=328 [M]$^{+\bullet}$ (100).
HPLC: 98.8% at 254 nm; 98.6% at 280 nm; t$_{MS}$=9.73 min, t$_M$(DMSO)=1.02 min (ACN/H$_2$O; 30:70); λ$_{max}$: 259 nm and 316 nm.

6-(4-Fluorophenyl)-4-(pyridin-2-ylthio)thieno[3,2-d]pyrimidine (8j)

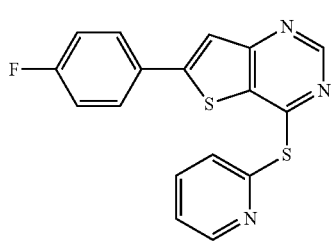

8j

Compound 8j was synthesized as described in method E; (Yield: 86.4%).
Mp=172-174° C.
IR (KBr): 3053 cm$^{-1}$ (C—H, aromat.).
$^1$H-NMR (CDCl$_3$, 400 MHz): 7.16-7.21 (m, 2H, ArH), 7.32-7.35 (ddd, J=2.13, 4.86, 6.82, 1H, ArH), 7.63 (s, 1H, ArH), 7.71-7.80 (m, with interference of 2H(m), 4H, ArH), 8.62-8.67 (d, J=4.6, 1H, ArH), 8.93 (s, 1H, ArH).
$^{13}$C-NMR (CDCl$_3$, 100 MHz): 116.4, 116.6, 119.6, 128.8, 128.9, 129.4, 137.4, 150.7, 154.5 (tert. C); 128.9, 129.0, 152.1, 152.2, 160.8, 161.0, 165.1 (quat. C).
Anal. calcd. for C$_{17}$H$_{10}$FN$_3$S$_2$: C, 60.16; H, 2.97; N, 12.38.
Found: C, 60.03; H, 2.90; N, 12.02.
MS (EI): m/z (%)=338 [M]$^{+\bullet}$ (100).
HPLC: 99.1% at 254 nm; 96.2% at 280 nm; t$_{MS}$=4.19 min, t$_M$(DMSO)=1.05 min (ACN/H$_2$O; 70:30); λ$_{max}$: 256 nm and 321 nm.

3-{[5-({6-[4-Fluorophenyl]thieno[3,2-d]pyrimidin-4-yl}thio)-1,3,4-oxadiazol-2-yl]methyl}-tetrahydro-thiophene-1,1-dioxide (8k)

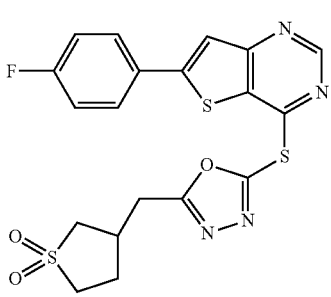

8k

Compound 8k was synthesized as described in method E; yellow powder (Yield: 82.0%).

Mp=180-182° C.

IR (KBr): 3050 cm$^{-1}$, 3003 cm$^{-1}$ (C—H, aromat.); 2942 cm$^{-1}$ (C—H, aliphat.).

$^1$H-NMR (DMSO-d$_6$, 600 MHz): 1.87-1.91 (m, 1H, aliphat. H), 2.32-2.38 (m, 1H, aliphat. H), 2.80-2.87 (m, 1H, aliphat. H), 2.90-2.95 (dd, J=10.95, 12.60, 1H, aliphat. H), 3.08-3.13 (m, 1H, aliphat. H), 3.24-3.28 (m, 3H, aliphat. H), 3.32 (s, 1H, aliphat H), 7.40-7.44 (m, 2H, ArH), 8.04-8.08 (m, 2H, ArH), 8.20 (s, 1H, ArH), 8.95 (s, 1H, ArH).

$^{13}$C-NMR (CDCl$_3$, 150.9 MHz): 28.2, 29.1, 51.8, 55.5 (sec. C); 34.2, 117.1, 117.2, 120.7, 129.9 (2C), 155.0 (tert. C); 128.2, 128.7, 152.9, 156.7, 157.6, 161.9, 163.1, 164.8, 169.2 (quat. C).

Anal. calcd. for C$_{19}$H$_{15}$FN$_4$O$_3$S$_3$: C, 49.34; H, 3.27; N, 12.11.

Found: C, 49.67; H, 2.99; N, 11.99.

MS (EI): m/z (%)=462 [M]$^{+\bullet}$ (10).

HPLC: 98.7% at 254 nm; 97.6% at 280 nm; t$_{MS}$=4.10 min, t$_M$ (DMSO)=1.02 min (ACN/H$_2$O; 50:50); λ$_{max}$: 244 nm and 315 nm.

2-Benzyl-5-{[6-(4-fluorophenyl)thieno[3,2-d]pyrimidin-4-yl]thio}-1,3,4-oxadiazole (8l)

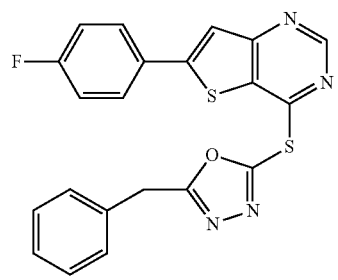

8l

Compound 8 l was synthesized as described in method E; yellow powder (Yield: 86.0%)

Mp=165-167° C.

IR (KBr): 3054 cm$^{-1}$ (C—H, aromat.).

$^1$H-NMR (CDCl$_3$, 400 MHz): 4.31 (s, 2H, aliphat. H), 7.17-7.22 (m, 2H, ArH), 7.29-7.33 (m, 5H, ArH), 7.63 (s, 1H, ArH), 7.68-7.73 (m, 2H, ArH), 8.86 (s, 1H, ArH).

$^{13}$C-NMR (DMSO-d$_6$, 100 MHz): 30.9 (sec. C); 116.5, 116.7, 120.2, 127.3, 128.8 (2C), 128.9 (2C), 129.3, 129.4, 154.5 (tert. C); 127.8, 128.2, 134.0, 152.4, 156.4, 157.2, 161.5, 162.3, 169.8 (quat. C).

Anal. calcd. for C$_{21}$H$_{13}$FN$_4$OS$_2$: C, 59.98; H, 3.12; N, 13.32.

Found: C, 59.91; H, 2.97; N, 13.21.

MS (EI): m/z (%)=420 [M]$^{+\bullet}$ (7).

HPLC: 99.0% at 254 nm; 98.4% at 280 nm; t$_{MS}$=7.58 min, t$_M$ (DMSO)=1.03 min (ACN/H$_2$O; 60:40); λ$_{max}$: 246 nm and 318 nm.

2-{[6-(4-Methoxyphenyl)thieno[3,2-d]pyrimidin-4-yl]thio}-5-phenyl-1,3,4-oxadiazole (8m)

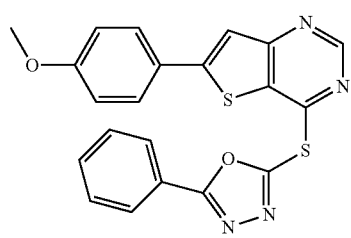

8m

Compound 8m was synthesized as described in method l, yellow needles (Yield: 57%).

Mp=213-215° C.

IR (KBr): 3059 cm$^{-1}$, 3003 cm$^{-1}$ (C—H, aromat.); 2956 cm$^{-1}$, 2848 cm$^{-1}$ (C—H, aliphat.).

$^1$H-NMR (CDCl$_3$-d$_1$, 600 MHz): 3.89 (s, 3H, CH$_3$), 6.99-7.03 (m, 2H, ArH), 7.51-7.56 (m, 2H, ArH), 7.56-7.60 (m, 1H, ArH), 7.61 (s, 1H, ArH), 7.69-7.73 (m, 2H, ArH), 8.09-8.12 (m, 2H, ArH), 8.87 (s, 1H, ArH).

$^{13}$C-NMR (CDCl$_3$-d$_1$, 150 MHz): 55.5 (prim. C); 114.8 (2C), 118.1, 127.3 (2C), 128.5 (2C), 129.2 (2C), 132.4, 154.6 (tert. C); 123.3, 124.8, 128.5, 154.5, 156.5, 156.8, 161.6, 161.9, 168.5 (quat. C).

MS (EI): m/z (%)=418 [M]$^{+\bullet}$ (14), 315 (100).

HRMS (EI): m/z [M]$^{+\bullet}$ calcd. 418.05527, found 418.05498.

HPLC: 96.1% at 254 nm; 96.5% at 280 nm; t$_{MS}$=5.53 min, t$_M$ (DMSO)=1.02 min (ACN/H$_2$O; 70:30); λ$_{max}$: 251 nm and 340 nm.

HPLC: 93.5% at 254 nm; t$_{MS}$=14.54 min, t$_M$ (DMSO)= 1.12 min (gradient, method 1).

2-(4-Chlorophenyl)-5-{[6-(4-methoxyphenyl)thieno [3,2-d]pyrimidin-4-yl]thio}-1,3,4-oxadiazole (8n)

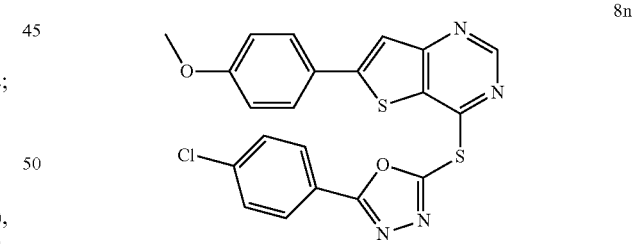

8n

Compound 8n was synthesized as described in method J, yellow powder (Yield: 88.5%).

Mp=221-223° C.

IR (KBr): 3074 cm$^{-1}$, 3052 cm$^{-1}$ (C—H, aromat.), 2939 cm$^{-1}$, 2844 cm$^{-1}$ (C—H, aliphat.).

$^1$H-NMR (CDCl$_3$-d$_1$, 600 MHz): 3.89 (s, 3H, CH$_3$), 7.01-7.03 (m, 2H, ArH), 7.51-7.52 (m, 2H, ArH), 7.61 (m, 1H, ArH), 7.71-7.72 (m, 2H, ArH), 8.04-8.05 (m, 2H, ArH), 8.87 (s, 1H, ArH).

$^{13}$C-NMR (CDCl$_3$-d$_1$, 150 MHz): 55.5 (prim. C); 114.8 (2C), 118.1, 128.4 (2C), 128.5 (2C), 129.6 (2C), 154.5 (tert. C); 121.8, 124.8, 128.5, 138.8, 154.5, 156.6, 156.7, 161.6, 161.9, 167.7 (quat. C).

MS (EI): m/z (%)=452 [M]+• (100).

Anal. calcd. for $C_{21}H_{13}ClN_4O_2S_2$: C, 55.69; H, 2.89; N, 12.37. Found: C, 55.81; H, 2.84; N, 12.13.

HPLC: 97.0% at 254 nm; 97.1% at 280 nm; $t_{MS}$=7.39 min, $t_M$(DMSO)=1.04 min (ACN/H$_2$O; 70:30); $\lambda_{max}$: 268 nm and 341 nm.

HPLC: 96.5% at 254 nm; $t_{MS}$=15.43 min, $t_M$ (DMSO)= 1.12 min (gradient, method 1).

2-{[6-(4-Methoxyphenyl)thieno[3,2-d]pyrimidin-4-yl]thio}-5-[4-(trifluoro-methyl)phenyl]-1,3,4-oxadiazole (8o)

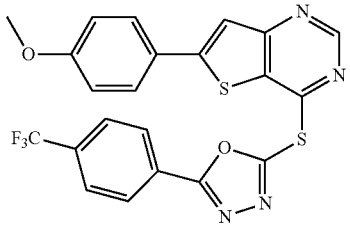

8o

Compound 8o was synthesized as described in method J, yellow powder (Yield: 61.5%).

Mp=227-228° C.

IR (KBr): 3074 cm$^{-1}$, 3053 cm$^{-1}$ (C—H, aromat.), 2941 cm$^{-1}$, 2842 cm$^{-1}$ (C—H, aliphat.).

$^1$H-NMR (CDCl$_3$-d$_1$, 600 MHz): 3.89 (s, 3H, CH$_3$), 7.01-7.03 (m, 2H, ArH), 7.62 (s, 1H, ArH), 7.71-7.73 (m, 2H, ArH), 7.80-7.81 (m, 2H, ArH), 8.23-8.25 (m, 2H, ArH), 8.86 (s, 1H, ArH).

$^{13}$C-NMR (CDC$_3$-d$_1$, 150 MHz): 55.5 (prim. C); 114.8 (2C), 118.1, 126.2 (2C), 127.6 (2C), 128.4 (2C), 154.7 (tert. C); 122.5, 124.3, 125.0, 126.5, 134.0, 154.6, 156.4, 157.4, 161.5, 162.0, 167.2 (quat. C).

MS (EI): m/z (%)=486 [M]+• (100).

Anal. calcd. for $C_{22}H_{13}F_3N_4O_2S_2$: C, 54.31; H, 2.61; N, 11.52. Found: C, 54.19; H, 2.65; N, 11.23.

HPLC: 97.7% at 254 nm; 97.4% at 280 nm; $t_MS$=4.28 min, $t_M$ (DMSO)=1.00 min (ACN/H$_2$O; 80:20); $\lambda_{max}$: 248 nm and 340 nm.

HPLC: 96.5% at 254 nm; $t_{MS}$=15.49 min, $t_M$ (DMSO)= 1.00 min (gradient, method 1).

2-{[6-(4-methoxyphenyl)thieno[3,2-d]pyrimidin-4-yl]thio}-5-(o-tolyl)-1,3,4-oxadiazole (8p)

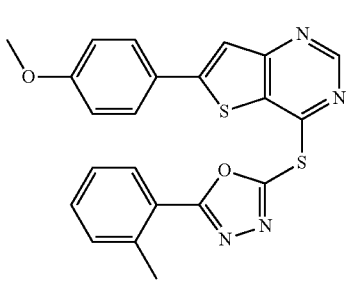

8p

Compound 8p was synthesized as described in method J, greenish powder (Yield: 76.4%).

Mp=184-186° C.

IR (KBr): 3075 cm$^{-1}$, 3046 cm$^{-1}$ (C—H, aromat.), 2927 cm$^{-1}$, 2841 cm$^{-1}$ (C—H, aliphat.).

$^1$H-NMR (CDCl$_3$-d$_1$, 600 MHz): 2.72 (s, 3H, CH$_3$), 3.89 (s, 3H, CH$_3$), 7.00-7.02 (m, 2H, ArH), 7.33-7.37 (m, 2H, ArH), 7.44-7.47 (m, 1H, ArH), 7.61 (s, 1H, ArH), 7.70-7.72 (m, 2H, ArH), 7.96-7.98 (m, 1H, ArH), 8.88 (s, 1H, ArH).

$^{13}$C-NMR (CDCl$_3$-d$_1$, 150 MHz): 22.0, 55.5 (prim. C); 114.8 (2C), 118.1, 126.3, 128.4 (2C), 129.3, 131.8, 131.9, 154.4 (tert. C); 122.5, 124.8, 128.5, 138.8, 154.5, 156.2, 156.9, 161.6, 161.9, 168.9 (quat. C).

MS (EI): m/z (%)=432 [M]+• (100).

Anal. calcd. for $C_{22}H_{16}N_4O_2S_2$: C, 61.09; H, 3.73; N, 12.95. Found: C, 61.33; H, 3.72; N, 12.71.

HPLC: 97.3% at 254 nm; 96.7% at 280 nm; $t_{MS}$=7.68 min, $t_M$(DMSO)=1.10 min (ACN/H$_2$O; 70:30); $\lambda_{max}$: 247 nm and 339 nm.

HPLC: 97.7% at 254 nm; $t_{MS}$=15.48 min, $t_M$ (DMSO)= 1.08 min (gradient, method 1).

2-(2,4-Dichlorophenyl)-5-{[6-(4-methoxyphenyl)thieno[3,2-d]pyrimidin-4-yl]thio}-1,3,4-oxadiazole (8q)

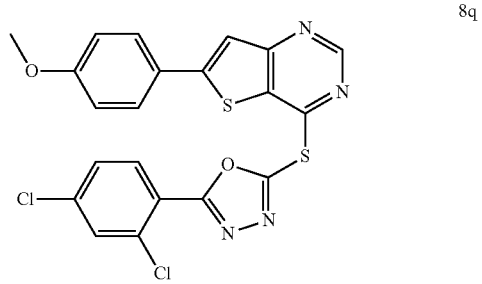 [SMILES: COc1ccc(-c2cc3ncnc(Sc4nnc(-c5ccc(Cl)cc5Cl)o4)c3s2)cc1]

8q

Compound 8q was synthesized as described in method J, yellow powder (Yield: 55.7%).

Mp=213-215° C.

IR (KBr): 3069 cm$^{-1}$, 3052 cm$^{-1}$, 3000 cm$^{-1}$ (C—H, aromat.), 2963 cm$^{-1}$, 2835 cm$^{-1}$ (C—H, aliphat.).

$^1$H-NMR (CDCl$_3$-d$_1$, 600 MHz): 3.89 (s, 3H, CH$_3$), 7.01-7.03 (m, 2H, ArH), 7.41-7.43 (dd, J=2.00, 8.40, 1H, ArH), 7.59 (d, J=2.03, 1H, ArH), 7.61 (s, 1H, ArH), 7.70-7.72 (m, 2H, ArH), 7.99-8.01 (d, J=8.53, 1H, ArH), 8.88 (s, 1H, ArH).

$^{13}$C-NMR (CDCl$_3$-d$_1$, 150 MHz): 55.5 (prim. C); 114.8 (2C), 118.1, 127.7, 128.5 (2C), 131.3, 132.1, 154.5 (tert. C); 121.2, 124.8, 128.7, 134.2, 138.8, 154.6, 156.4, 157.5, 161.7, 162.0, 166.1 (quat. C).

MS (EI): m/z (%)=486 [M]+• (7), 315 (100).

Anal. calcd. for $C_{21}H_{12}Cl_2N_4O_2S_2$: C, 51.75; H, 2.48; N, 11.50. Found: C, 51.86; H, 2.47; N, 11.28.

HPLC: 97.7% at 254 nm; 97.9% at 280 nm; $t_{MS}$=5.37 min, (ACN/H$_2$O; 80:20); $\lambda_{max}$: 250 nm and 340 nm.

HPLC: 98.4% at 254 nm; $t_{MS}$=17.64 min, $t_M$ (DMSO)= 1.09 min (gradient, method 1).

4-{[5-(4-Chlorophenyl)-1,3,4-oxadiazol-2-yl]thio}-6-(4-methoxyphenyl)thieno[3,2-d]pyrimidin-2-amine (8r)

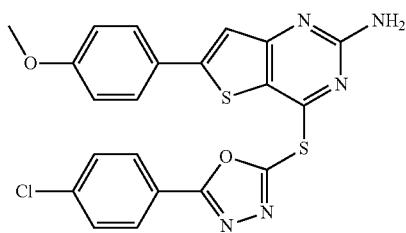

Compound 8r was synthesized as described in method J, beige powder (Yield: 48.4%).

Mp=206-208° C.

IR (KBr): 3412 cm$^{-1}$ (NH$_2$); 3175 cm$^{-1}$ (C—H, aromat.).

$^1$H-NMR (DMSO-d$_6$, 600 MHz): 3.83 (s, 3H, CH$_3$), 6.79 (s, 2H, NH$_2$), 7.05-7.08 (m, 2H, ArH), 7.57 (s, 1H, ArH), 7.69-7.71 (m, 2H, ArH), 7.79-7.81 (m, 2H, ArH), 8.06-8.08 (m, 2H, ArH).

$^{13}$C-NMR (DMSO-d$_6$, 150 MHz): 55.3 (prim. C); 114.6 (2C), 117.2, 127.9 (2C), 128.6 (2C), 129.7 (2C) (tert. C); 116.1, 121.6, 124.5, 137.3, 152.7, 155.9, 157.0, 160.8, 161.3, 164.2, 166.7 (quat. C).

MS (EI): m/z (%)=467 [M]$^{+\bullet}$ (9), 257 (100).

HRMS (EI): m/z [M]$^{+\bullet}$ calcd. 467.02720, found 467.02695.

HPLC: 99.6% at 254 nm; 99.7% at 280 nm; t$_{MS}$=6.27 min, (ACN/H$_2$O; 70:30); λ$_{max}$: 260 nm and 333 nm.

HPLC: 94.9% at 254 nm; t$_{MS}$=15.55 min, t$_M$ (DMSO)=1.02 min (gradient, method 1).

2-[(8-Phenyl-9H-purin-6-yl)thio]-5-(pyridin-4-yl)-1,3,4-oxadiazole (8s)

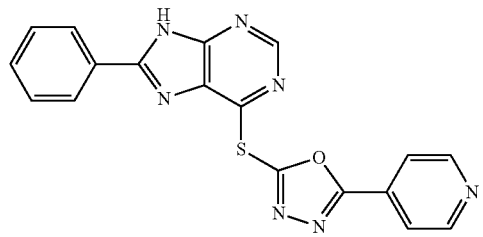

Compound 8s was synthesized as described in method K; white solid (Yield: 41%).

Mp=250-251° C.

IR (KBr): 3434 cm$^{-1}$ (NH).

$^1$H-NMR (DMSO-d$_6$, 400 MHz): δ (ppm)=7.43 (m, 2H, ArH), 7.52 (t, 1H, J=7.46 Hz, ArH), 7.98 (d, 2H, J=7.49 Hz, ArH), 8.05 (m, 2H, ArH), 8.71 (s, 1H, ArH), 8.87 (m, 2H, ArH), 14.26 (m, 1H, NH).

$^{13}$C-NMR (DMSO-d$_6$, 100 MHz): d (ppm)=120.2 (2C), 126.8 (2C), 128.8 (2C), 131.4, 151.1 (2C), 151.4 (tert. C); 128.0, 129.9, 130.8, 152.6, 153.0, 153.2, 158.2, 165.8 (quart. C).

MS (EI): m/z (%)=373 [M]$^{+\bullet}$ (10), 269 (100), 195 (22), 78 (23).

HRMS (EI): m/z [M]$^{+\bullet}$ calcd. 373.07403, found 373.07403.

HPLC: 99.4% at 254 nm and 97.9% at 280 nm (ACN/H$_2$O; 40:60), t$_{MS}$=3.8 min, t$_M$=1.05 min, λ$_{max}$=242 and 310 nm.

HPLC: 99.4% at 254 nm; t$_{MS}$=9.05 min, t$_M$=1.25 min (gradient, method 2).

2-Benzyl-5-[(8-phenyl-9H-purin-6-yl)thio]-1,3,4-oxadiazole (8t)

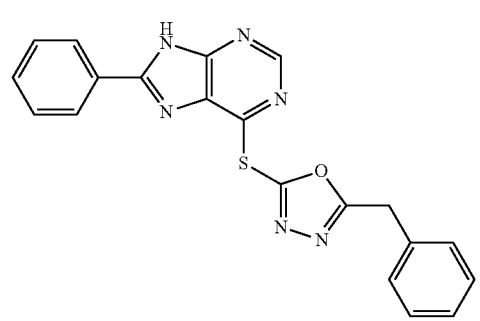

Compound 8t was synthesized as described in method L; white solid (Yield: 29%).

Mp=198-199° C.

IR (KBr): 3434 cm$^{-1}$ (NH).

$^1$H-NMR (DMSO-d$_6$, 400 MHz): δ (ppm)=4.41 (s, 2H, CH$_2$), 7.21-7.35 (m, 5H, ArH), 7.59 (m, 3H, ArH), 8.14 (m, 2H, ArH), 8.66 (s, 1H, ArH), 14.26 (s, 1H, NH).

$^{13}$C-NMR (DMSO-d$_6$, 100 MHz): d (ppm)=30.1 (CH$_2$), 127.1, 127.11 (2C), 128.5 (2C), 128.7 (2C), 129.1 (2C), 131.4, 151.3 (tert. C), 128.2, 131.1, 133.9, 152.2, 152.6, 153.4, 156.8, 169.2.

MS (EI): m/z (%)=386 [M]+(18), 269 (100), 195 (16), 91 (57).

HRMS (EI): m/z [M]$^{+\bullet}$ calcd. 386.09443, found 386.09466.

HPLC: 99.6% at 254 nm and 99.0% at 280 nm (ACN/H$_2$O; 50:50), t$_{MS}$=4.02 min, t$_M$=1.05 min, λ$_{max}$: 240 nm and 310 nm.

HPLC: 98.2% at 254 nm; t$_{MS}$=10.55 min, t$_M$=1.25 min (gradient, method 2).

2-(Furan-2-yl)-5-[(8-phenyl-9H-purin-6-yl)thio]-1,3,4-oxadiazole (8u)

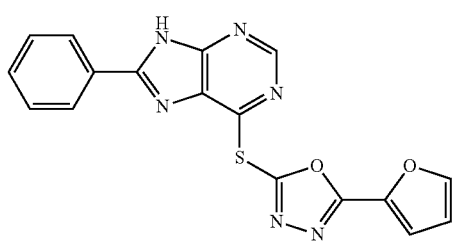

Compound 8u was synthesized as described in method L; yellow solid (Yield: 36%).

Mp=224-225° C.

IR (KBr): 3426 cm$^{-1}$.

$^1$H-NMR (DMSO-d$_6$, 400 MHz): δ (ppm)=6.84 (m, 1H, J=1.79 Hz, ArH), 7.45-7.57 (m, 4H, ArH), 8.03 (m, 2H, ArH), 8.14 (m, 1H, J=1.81 Hz, ArH), 8.70 (s, 1H, ArH), 14.26 (s, 1H, NH).

$^{13}$C-NMR (DMSO-d$_6$, 100 MHz): d (ppm)=112.8, 115.7, 126.9 (2C) 128.9 (2C), 131.5, 147.6 151.4 (tert. C), 128.1, 130.8, 138.2 152.8, 153.2, 156.0 160.1 (quart. C).

MS (EI): m/z (%)=362 [M]$^{+\bullet}$ (9), 269 (100), 195 (16).

HRMS (EI): m/z [M]$^{+\bullet}$ calcd. 362.05805, found 362.05899.

HPLC: 98.5% at 254 nm and 98.9% at 280 nm (ACN/H$_2$O; 40:60), t$_{MS}$=5.70 min, t$_M$=1.05 min, λ$_{max}$: 241 nm, 284 nm and 309 nm.

HPLC: 98.4% at 254 nm; t$_{MS}$=9.70 min, t$_M$=1.25 min (gradient, method 2).

2-[(8-Phenyl-9H-purin-6-yl)thio]-5-[4-(trifluoromethyl)phenyl]-1,3,4-oxadiazole (8v)

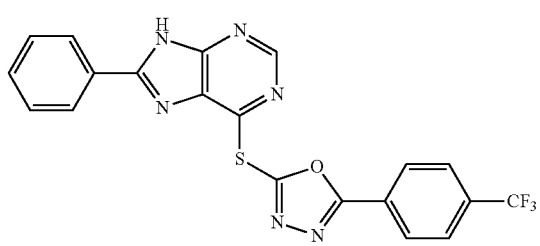

8v

Compound 8v was synthesized as described in method L; yellow solid (Yield: 49%).

Mp=256-257° C.

IR (KBr): 3466 cm$^1$ (NH).

$^1$H-NMR (DMSO-d$_6$, 400 MHz): δ (ppm)=7.42 (m, 2H, ArH), 7.52 (m, 1H, ArH), 7.99 (m, 4H, ArH), 8.32 (d, 4H, J=8.02, ArH), 8.71 (s, 1H, ArH), 14.26 (s, 1H, NH).

$^{13}$C-NMR (DMSO-d$_6$, 100 MHz): d (ppm)=126.5, 126.8, 127.6 (2C), 128.8 (2C), 131.4, 151.4 (tert. C), 122.6, 124.4, 128.1, 130.9, 131.9, 132.1, 152.7, 152.9, 153.2, 157.7, 166.2 (quart. C).

MS (EI): m/z (%)=440 [M]$^{+\bullet}$ (9), 269 (100), 145 (30).

HRMS (EI): m/z [M]+$^{+\bullet}$ calcd. 440.06617, found 440.06672.

HPLC: 99.5% at 254 nm and 99.5% at 280 nm (ACN/H$_2$O; 60:40), t$_{MS}$=4.47 min t$_M$=1.05 min, λ$_{max}$: 244 nm and 310 nm.

HPLC: 98.7% at 254 nm; t$_{MS}$=12.55 min, t$_M$=1.25 min (gradient, method 2).

Protein Kinase Activity Assay

The effect of the thioether derivatives 8a-v and 9a-i was tested on recombinant, human protein kinases. All protein kinases were expressed in Sf9 insect cells as human recombinant GST-fusion proteins or as His-tagged proteins by means of the baculovirus expression system. Protein kinases were purified by affinity chromatography using either GSH-agarose or Ni-NTH-agarose. The purity and identity of each was checked by SDS-PAGE/silver staining and by western blot analysis with specific antibodies.

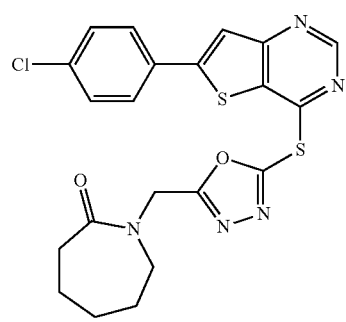

9a

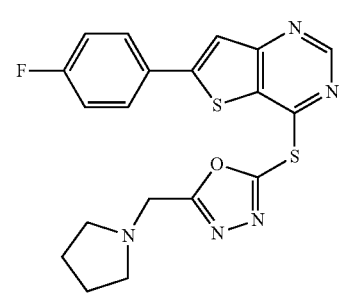

9b

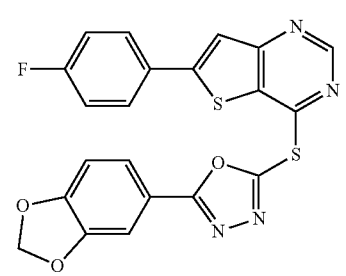

9c

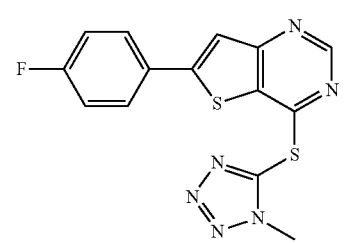

9d

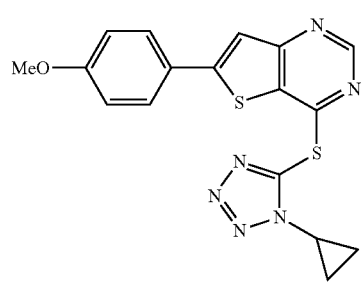

9e

9f
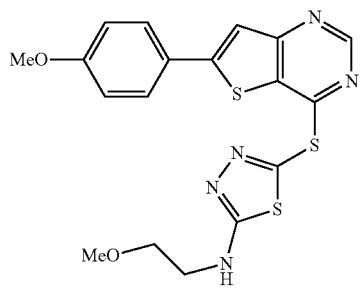

9g
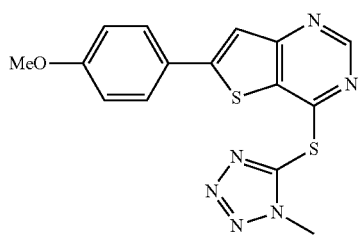

9h
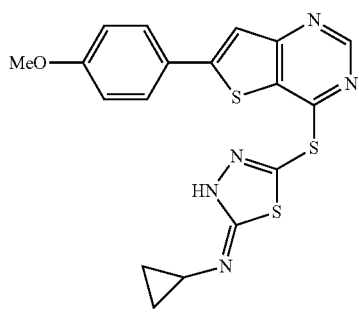

9i
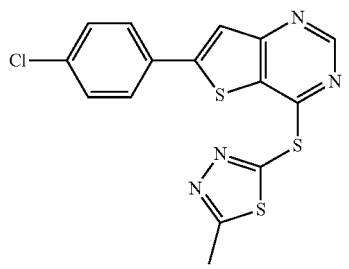

A proprietary protein kinase assay ($^{33}$PanQinase® Activity Assay) was used for measuring the kinase activity. All kinase assays were performed in 96-well FlashPlates™ in a 50 µl reaction volume. The assay for all enzymes contained 60 mM HEPES-NaOH, pH 7.5, 3 mM MgCl$_2$, 3 mM MnCl$_2$, 3 µM Na-orthovanadate, 1.2 mM DTT, 50 µg/ml PEG$_{20000}$ and 1 µM [γ-$^{33}$P]-ATP (approx. 5×10$^5$ cpm per well).

The reaction cocktails were incubated at 30° C. for 80 minutes. The reaction was stopped with 50 µl of 2% (v/v) H$_3$PO$_4$, plates were aspirated and washed two times with 200 µl of 0.9% (w/v) NaCl. Incorporation of $^{33}$P$_i$ was determined with a microplate scintillation counter. All assays were performed with a BeckmanCoulter/Sagian robotic system.

The results of the protein kinase activity assay are depicted in Table 1.

Thioether derivatives 8a-v and 9a-i show excellent IC$_{50}$ values. In particular, compounds 9a, 9c, 9h, 8a, 8e, 8f, 8h, 8l-r and 8v advantageously show IC$_{50}$ values lower than 1 µM on at least one kinase selected from ALK, AXL, FAK, KIT wt, IGF1-R, PIM1, PRK1, SRC and VEGF-R2. Moreover, Compounds 9a-c, 9e-h, 8a-h and 8j-r and 8v advantageously display a beneficial activity profile by inhibiting at least two kinases from at least two different molecular mechanisms of tumor progression with IC$_{50}$ values lower than 10 µM.

Further compounds of the present invention encompassed by general formula (3) are:

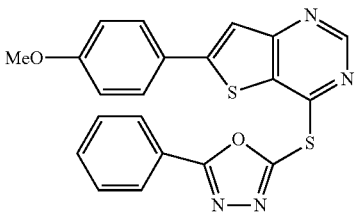

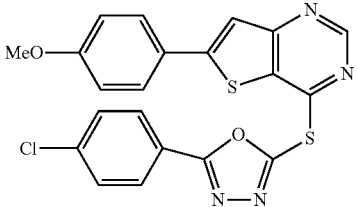

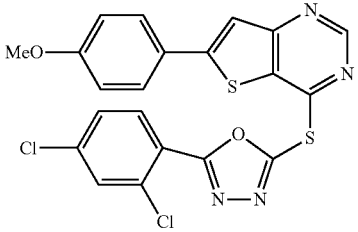

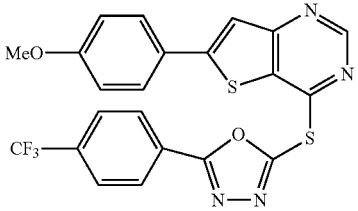

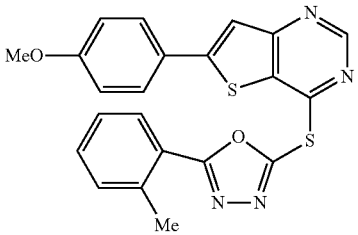

TABLE 1

IC50 values (in M) of thioether derivatives 8a-v and 9a-i

| Example No. | Compound | Mr | ALK IC50 (M) | AXL IC50 (M) | FAK IC50 (M) | KIT wt IC50 (M) | IGF1-R IC50 (M) | PIM1 IC50 (M) | PRK1 IC50 (M) | SRC IC50 (M) | VEGF-R2 IC50 (M) |
|---|---|---|---|---|---|---|---|---|---|---|---|
| 1 | 9a | 471.98 | 2.16E-06 | 1.63E-06 | 8.93E-06 | 6.08E-07 | | | | | |
| 2 | 9b | 413.49 | 3.03E-06 | 6.09E-06 | 1.50E-05 | 6.48E-06 | | | | | |
| 3 | 9c | 450.47 | 9.35E-07 | 6.56E-06 | 3.52E-06 | 4.92E-06 | | | | | |
| 4 | 9d | 344.39 | 1.36E-05 | 2.89E-05 | 1.36E-05 | 2.41E-06 | | | | | |
| 5 | 9e | 382.46 | 2.76E-06 | 9.76E-06 | 7.89E-06 | 1.30E-06 | | | | | |
| 6 | 9f | 431.55 | 3.51E-06 | 5.20E-06 | 1.67E-05 | 8.04E-07 | | | | | |
| 7 | 9g | 356.43 | 2.37E-06 | 5.80E-06 | 5.99E-06 | 1.02E-06 | | | | | |
| 8 | 9h | 413.54 | 2.72E-06 | 1.01E-05 | 1.05E-05 | 8.73E-07 | | | | | |
| 9 | 9i | 376.91 | 1.50E-05 | 4.17E-05 | >1E-04 | 1.25E-06 | | | | | |
| 10 | 8a | 406.46 | 9.87E-07 | 3.16E-06 | | 1.04E-06 | | | | | |
| 11 | 8b | 407.44 | 2.94E-06 | 2.64E-06 | | 1.74E-06 | | | | | |
| 12 | 8c | 387.45 | 6.54E-06 | 1.23E-06 | | 2.76E-06 | | | | | |
| 13 | 8d | 429.49 | 5.59E-06 | 7.66E-06 | | 3.85E-06 | | | | | |
| 14 | 8e | 474.45 | 9.77E-07 | 2.51E-06 | 1.96E-06 | | 1.03E-06 | 8.68E-06 | 1.54E-05 | 5.40E-07 | 1.41E-06 |
| 15 | 8f | 450.51 | 6.51E-07 | 3.20E-06 | 1.28E-06 | | 1.27E-06 | 1.04E-05 | 1.46E-05 | 4.87E-07 | 1.47E-06 |
| 16 | 8g | 386.46 | 2.37E-06 | 6.19E-06 | 4.82E-06 | | 3.28E-06 | 2.29E-05 | | 2.51E-06 | 4.07E-06 |
| 17 | 8h | 406.42 | 1.03E-06 | 2.94E-06 | 2.04E-06 | | 1.37E-06 | 1.13E-05 | 3.39E-05 | 6.81E-07 | 1.84E-06 |
| 18 | 8i | 328.29 | 2.37E-05 | 4.15E-05 | 2.21E-05 | | 2.31E-05 | 1.11E-05 | 8.61E-05 | 1.10E-05 | 2.08E-05 |
| 19 | 8j | 339.41 | 6.63E-06 | 2.26E-05 | 9.08E-06 | | 9.15E-06 | | 4.73E-05 | 6.35E-06 | 9.69E-06 |
| 20 | 8k | 462.54 | 2.95E-06 | 4.58E-06 | 5.76E-06 | | 7.65E-06 | 2.63E-05 | | 2.62E-06 | 2.05E-06 |
| 21 | 8l | 420.48 | 1.15E-06 | 3.14E-06 | 3.01E-06 | | 1.50E-06 | 1.37E-05 | 3.80E-05 | 8.75E-07 | 2.24E-06 |
| 22 | 8m | 418.49 | 9.70E-07 | 9.40E-07 | 8.30E-07 | | | | | 3.20E-08 | |
| 23 | 8n | 452.94 | 1.00E-06 | 2.70E-06 | 1.40E-06 | | | | | 5.50E-07 | |
| 24 | 8o | 486.49 | 8.8E-07 | 2.4E-06 | 1.7E-06 | | | | | 8.4E-07 | |
| 25 | 8p | 432.52 | 9.2E-07 | 1.9E-06 | 1.3E-06 | | | | | 6.8E-07 | |
| 26 | 8q | 487.38 | 1.30E-06 | 2.20E-06 | 1.50E-06 | | | | | 8.00E-07 | |
| 27 | 8r | 467.95 | 7.3E-07 | 1.2E-06 | 9.0E-07 | | | | | 6.5E-07 | |
| 28 | 8s | 373.39 | 2.7E-05 | 2.4E-05 | 2.6E-05 | | | | | 1.9E-05 | |
| 29 | 8t | 386.43 | 7.6E-05 | >1E-04 | 4.3E-05 | | | | | 3.2E-05 | |
| 30 | 8u | 362.37 | 2.2E-05 | 4.0E-05 | 2.3E-05 | | | | | 1.1E-05 | |
| 31 | 8v | 440.4 | 8.6E-07 | >1E-04 | 9.3E-07 | | | | | 7.0E-07 | |

REFERENCES

[1] Romagnoli, R., Baraldi, P. G., Carrion, M. D., Cara, C. L., Cruz-Lopez, O., Preti, D., Tolomeo, M., Grimaudo, S., Cristina, A. D., Zonta, N., Balzarini, J., Brancale, A., Sarkar, T., Hamel, E.: Design, synthesis, and biological evaluation of thiophene analogues of chalcones. Bioorg. Med. Chem. 2008, 16, 5367-5376.

[2] Romagnoli, R., Baraldi, P. G., Remusat, V., Carrion, M. D., Cara, C. L., Preti, D., Fruttarolo, F., Pavani, M. G., Tabrizi, M. A., Tolomeo, M., Grimaudo, S., Balzarini, J., Jordan, M. A., Hamel, E.: Synthesis and biological evaluation of 2-(3',4',5'-trimethoxybenzoyl)-3-amino 5-aryl thiophenes as a new class of tubulin inhibitors. J. Med. Chem. 2006, 49, 6425-6428.

[3] Hartmann, H., Liebscher, J.: A simple method for the synthesis of 5-aryl-3-amino-2-alkoxycarbonylthiophenes. Synthesis 1984, 275-276.

[4] Thrash, T., Cabell, L. A., Lohse, D., Budde, R. J. A. (2006). Small molecule thienopyrimidine-based protein tyrosine kinase inhibitors; US 2006/0004002 A1.

[5] Munchhof, M. J., Sobolov, S. B., Marx, M. A. (2002). Thienopyrimidine and thienopyridine derivatives useful as anticancer agents; WO1998IB01 691 19981022.

[6] Manjunatha, K., Poojary, B., Lobo, P. L., Femandes, J., Kumari, N. S.: Synthesis and biological evaluation of some 1,3,4-oxadiazole derivatives. Eur. J. Med. Chem. 2010, 45, 5225-5233.

[7] Farghaly, A. R., El-Kashef, H.: Synthesis of some new azoles with antiviral potential. Arkivoc 2006, 76-90.

[8] Jansen, M., Rabe, H., Strehle, A., Dieler, S., Debus, F., Dannhardt, G., Akabas, M., Lüddens, H.: Synthesis of GABA A receptor agonists and evaluation of their α-subunit selectivity and orientation in the GABA binding site. J. Med. Chem. 2008, 51, 4430-4448.

[9] Ren, W.-Y., Rao, K. V. B., Klein, R. S.: Convenient synthesis of substituted 3-aminothiophene-2-carbonitriles from α-acetylenic nitriles and their conversion to thieno [3,2-d]pyrimidines. J. Heterocycl. Chem. 1986, 23, 1757-1763.

[10] Ghani, U., Ullah, N.: New potent inhibitors of tyrosinase: Novel clues to binding of 1,3,4-thiadiazole-2(3H)-thiones, 1,3,4-oxadiazole-2(3H)-thiones, 4-amino-1,2,4-triazole-5(4H)-thiones, and substituted hydrazides to the dicopper active site. Bioorg. Med. Chem. 2010, 18, 4042-4048.

[11] Wang, Y.-T., Tang, G.-M., Ma, W.-Y., Wan, B. Z.: Synthesis and characterization of two new coordination supramolecular structures from a versatile unsymmetric 5-(4-pyridyl)-1,3,4-thiadiazole-2-thione (Hpot) ligand. Polyhedron 2007, 26, 782-790.

[12] Hosur, M. C., Talawar, M. B., Laddi, U. V., Bennur, R. S., Bennur, S. C.: Synthesis and antimicrobial activities of some new 1,3,4-oxadiazoles. Indian J. Heterocycl. Chem. 1994, 3, 237-242.

[13] Li, Y., Liu, J., Zhang, H., Yang, X., Liu, Z.: Stereoselective synthesis and fungicidal activities of (E)-α-(methoxyimino)-benzeneacetate derivatives containing 1,3,4-oxadiazole ring. Stereoselective synthesis and fungicidal activities of (E)-α-(methoxyimino)-benzeneacetate derivatives containing 1,3,4-oxadiazole ring. Bioorg. Med. Chem. Lett. 2006, 16, 2278-2282.

[14] Zhao, G., Xu, W., Wang, Y., Tang, L., Wang, Z., Zou, M., Liu, W., Zhang, S., Tan, C., Liu, B. (2009). Preparation of thioglucosides as SGLT2 inhibitors and antidiabetics. Faming Zhuanli Shenqing CN 101445528 A 20090603.

[15] Kajiwara, M., Miyoshi, M., Onodera, K., Sakamoto, E. (1988). Silver halide photographic material containing hydroquinone derivative and azole compound for rapid processing; EP 0 255 402 A2.

[16] Liebscher, J., Neumann, B., Hartmann, H.: Eine einfache Synthese von β-Chlorzimtsäurenitrilen nach einer modifizierten Vilsmeyer-Haack-Arnold-Reaktion. *J. prakt. Chem.* 1983, 325, 915-918.

[17] Abdillahi, I., Kirsch, G.: Synthesis of a novel series of thieno[3,2-d]pyrimidin-4-(3H)-ones. *Synthesis* 2010, 1428-1430.

[18] Savall, B. M., Gomez, L., Chavez, F., Curtis, M., Meduna, S. P., Kearney, A., Dunford, P., Cowden, J., Thurmond, R. L., Grice, C., Edwards, J. P.: Tricyclic aminopyrimidine histamine H4 receptor antagonists. *Bioorg. Med. Chem. Lett.* 2011, 21, 6577-6581.

[19] Edwards, J. P., Neff, D. K., Smith, D. M., Venable, J. D. (2009) Preparation of thieno- and furo-pyrimidine modulators of the histamine H4 receptor. US 2009/0075970 A1.

[20] Ife, R. J., Brown, T. H., Blurton, P., Keeling, D. J., Leach, C. A., Meeson, M. L., Parsons, M. E., Theobald, C. J.: Reversible Inhibitors of the Gastric (H+/K+)-ATPase. 5. Substituted 2,4-Diaminoquinazolines and Thienopyrimidines. *J. Med. Chem.* 1995, 38, 2763-2773.

[21] Jang, M.-Y., Jonghe, S. D., Segers, K., Anné, J., Herdewijn, P.: Synthesis of novel 5-amino-thiazolo[4,5-d]pyrimidines as *E. coli* and *S. aureus* SecA inhibitors. *Bioorg. Med. Chem.* 2011, 19, 702-714.

[22] Henderson, E. A., Bavetsias, V., Theti, D. S., Wilson, S. C., Clauss, R., Jackman, A. L.: Targeting the α-folate receptor with cyclopenta[g]quinazoline-based inhibitors of thymidylate synthase. *Bioorg. Med. Chem.* 2006, 14, 5020-5042.

[23] Mndzhoyan, A. L.; Tatevosyan, G. T.; Agbalyan, S. G.; Divanyan, N. M.: Furan derivatives. XVI. Some furan derivatives containing bivalent sulfur. *Dokl. Akad. Nauk Arm. SSR* 1957, 25, 207-211.

[24] Ibrahim, N.; Legraverend, M.: High-yielding two-step synthesis of 6,8-disubstituted N-9-unprotected purines. *J. Comb. Chem.* 2009, 11, 658-666.

[25] Goswami, B. N., Borthakur, N., Ghosh, A. C.: 1,3,4-Oxadiazolethiol as acyl-transfer reagent in acylation of amines: a one-pot reaction. *J. Chem. Research* 1998, (S), 268-269.

The invention claimed is:

1. A protein kinase inhibitor according to general formula (1) or a pharmaceutically acceptable salt thereof:

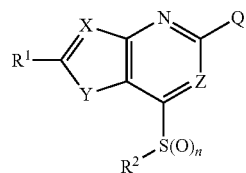

Formula (1)

wherein X is CH;
Y is S;
Z is N;
$R^1$ is selected from a substituted or unsubstituted aryl group and a substituted or unsubstituted heteroaryl group;

$R^2$ is the following residue:

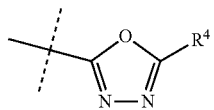

wherein $R^4$ is selected from linear alkyl group with a chain length of $C_1$-$C_6$ or branched alkyl group with $C_3$-$C_6$ carbon atoms, one or more hydrogen atom(s) of which may be replaced by a substituent selected from halogen, aryl, heteroaryl, hydroxyl, alkoxy, carboxylic acid, acyl, amino, cyano, nitro, alkylsulfanyl, alkylsulfinyl, alkylsulfonyl, sulfamoyl, sulfoximino, trihalogenmethoxy, and trihalogenmethyl; a phenyl group or a naphthyl group, one or more hydrogen atom(s) of which may be replaced by a substituent selected from alkyl, halogen, aryl, heteroaryl, hydroxyl, alkoxy, carboxylic acid, acyl, amino, alkylamino, cyano, nitro, alkylsulfanyl, alkylsulfinyl, alkylsulfonyl, sulfamoyl, sulfoximino, trihalogenmethoxy, and trihalogenmethyl; and benzofuryl, benzimidazolyl, benzisoxazolyl, benzothiazolyl, cinnolinyl, imidazolyl, indazolyl, indolizinyl, indolyl, isoindolyl, isoquinolyl, isoxazolyl, naphthyridyl, oxadiazolyl, oxazolyl, phthalazinyl, pyrazolyl, pyrazinyl, pyridazinyl, pyridinyl, pyrimidinyl, quinazolyl, quinolyl, quinoxalyl, thiazolyl, tetrazolyl, thiadiazolyl, or triazolyl, one or more hydrogen atom(s) of which may be replaced by a substituent selected from alkyl, halogen, aryl, heteroaryl, hydroxyl, alkoxy, carboxylic acid, acyl, amino, alkylamino, cyano, nitro, alkylsulfanyl, alkylsulfinyl, alkylsulfanyl, sulfamoyl, sulfoximino, trihalogenmethoxy, and trihalogenmethyl;

n is selected from 0, 1 and 2; and

Q is selected from H and a substituted or unsubstituted amino group.

2. The protein kinase inhibitor or a pharmaceutically acceptable salt thereof according to claim 1, wherein $R^1$ is the following residue:

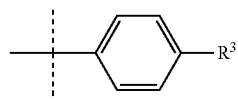

wherein $R^3$ is selected from F, Cl, Br, I, substituted or unsubstituted alkyl, substituted or unsubstituted alkoxy and hydroxyl.

3. The protein kinase inhibitor or a pharmaceutically acceptable salt thereof according to claim 2, wherein $R^3$ is F.

4. The protein kinase inhibitor or a pharmaceutically acceptable salt thereof according to claim 1, wherein the protein kinase inhibitor is a thioether derivative of the general formula (3):

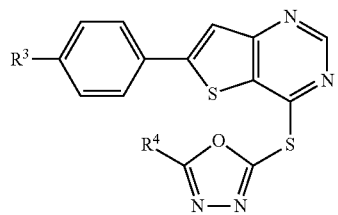

Formula (3)

wherein R³ is selected from F, Cl, Br, I, substituted or unsubstituted alkyl, substituted or unsubstituted alkoxy and hydroxyl.

5. A pharmaceutical composition, comprising the protein kinase inhibitor or the pharmaceutically acceptable salt thereof according to claim 1.

6. A method for producing a protein kinase inhibitor according to general formula (4):

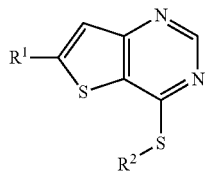

Formula (4)

wherein the method comprises reacting a compound of general formula (5)

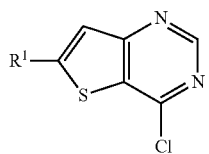

Formula (5)

with R²—SH in the presence of a base, wherein R¹ is selected from a substituted or unsubstituted aryl group and a substituted or unsubstituted heteroaryl group and R² is the following residue:

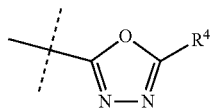

wherein R⁴ is selected from linear alkyl group with a chain length of $C_1$-$C_6$ or branched alkyl group with $C_3$-$C_6$ carbon atoms, one or more hydrogen atom(s) of which may be replaced by a substituent selected from halogen, aryl, heteroaryl, hydroxyl, alkoxy, carboxylic acid, acyl, amino, cyano, nitro, alkylsulfanyl, alkylsulfinyl, alkylsulfonyl, sulfamoyl, sulfoximino, trihalogenmethoxy, and trihalogenmethyl; a phenyl group or a naphthyl group, one or more hydrogen atom(s) of which may be replaced by a substituent selected from alkyl, halogen, aryl, heteroaryl, hydroxyl, alkoxy, carboxylic acid, acyl, amino, alkylamino, cyano, nitro, alkylsulfanyl, alkylsulfinyl, alkylsulfonyl, sulfamoyl, sulfoximino, trihalogenmethoxy, and trihalogenmethyl; and benzofuryl, benzimidazolyl, benzisoxazolyl, benzothiazolyl, cinnolinyl, imidazolyl, indazolyl, indolizinyl, indolyl, isoindolyl, isoquinolyl, isoxazolyl, naphthyridyl, oxadiazolyl, oxazolyl, phthalazinyl, pyrazolyl, pyrazinyl, pyridazinyl, pyridinyl, pyrimidinyl, quinazolyl, quinolyl, quinoxalyl, thiazolyl, tetrazolyl, thiadiazolyl, or triazolyl, one or more hydrogen atom(s) of which may be replaced by a substituent selected from alkyl, halogen, aryl, heteroaryl, hydroxyl, alkoxy, carboxylic acid, acyl, amino, alkylamino, cyano, nitro, alkylsulfanyl, alkylsulfinyl, alkylsulfonyl, sulfamoyl, sulfoximino, trihalogenmethoxy, and trihalogenmethyl.

7. The pharmaceutical composition according to claim 5 comprising one or more of a pharmaceutically acceptable carrier and an excipient.

* * * * *